(12) United States Patent
Smolinski

(10) Patent No.: US 10,669,236 B2
(45) Date of Patent: Jun. 2, 2020

(54) SOLID FORMS OF 2-(5-(4-(2-MORPHOLINO-ETHOXY)PHENYL)PYRIDIN-2-YL)-N-BENZYLACETAMIDE

(71) Applicant: Athenex HK Innovative Limited, Hong Kong (HK)

(72) Inventor: Michael P. Smolinski, Amherst, NY (US)

(73) Assignee: Athenex HK Innovative Limited, Sha Tin (HK)

( * ) Notice: Subject to any disclaimer, the term of this patent is extended or adjusted under 35 U.S.C. 154(b) by 0 days.

(21) Appl. No.: 16/124,281

(22) Filed: Sep. 7, 2018

(65) Prior Publication Data

US 2019/0071402 A1 Mar. 7, 2019

Related U.S. Application Data

(60) Provisional application No. 62/555,390, filed on Sep. 7, 2017.

(51) Int. Cl.
*C07D 213/56* (2006.01)
*A61K 31/4418* (2006.01)

(52) U.S. Cl.
CPC ........ *C07D 213/56* (2013.01); *C07B 2200/13* (2013.01)

(58) Field of Classification Search
CPC .................... C07B 2200/13; C07D 213/56
See application file for complete search history.

(56) References Cited

U.S. PATENT DOCUMENTS

| | | |
|---|---|---|
| 4,522,811 A | 6/1985 | Eppstein et al. |
| 7,300,931 B2 | 11/2007 | Hangauer |
| 7,851,470 B2 | 12/2010 | Hangauer et al. |
| 7,939,529 B2 | 5/2011 | Hangauer et al. |
| 2009/0318450 A1 | 12/2009 | Hangauer et al. |

FOREIGN PATENT DOCUMENTS

| | | |
|---|---|---|
| CN | 106810490 A | 6/2017 |
| WO | WO 2008-002676 A2 | 1/2008 |
| WO | WO 2015-069217 A1 | 5/2015 |

OTHER PUBLICATIONS

Harada, K. et al., "Identification of KX2-391 as an inhibitor of HBV transcription by a recombinant HBV-based screening assay", Antiviral Research, 2017, vol. 144, pp. 138-146.

*Primary Examiner* — Susanna Moore
(74) *Attorney, Agent, or Firm* — Cooley LLP; Heidi A. Erlacher; Chen Chen

(57) ABSTRACT

The present application provides solid Forms A, B, and C of 2-(5-(4-(2-morpholinoethoxy)phenyl)pyridin-2-yl)-N-benzylacetamide, and methods of preparing and using same. The compounds disclosed herein may be used in the treatment or prevention of a disease or condition in which a tyrosine kinase plays a role.

10 Claims, 37 Drawing Sheets

SOLID FORMS OF 2-(5-(4-(2-MORPHOLINO-ETHOXY)PHENYL)PYRIDIN-2-YL)-N-BENZYLACETAMIDE

RELATED APPLICATION

This application claims priority to, and the benefit of, U.S. Provisional Application No. 62/555,390, filed on Sep. 7, 2017, the entire contents of which are incorporated herein by reference.

BACKGROUND

Signal transduction is any process by which a cell converts one kind of signal or stimulus into another. Protein kinases are involved in signal transduction. A tyrosine kinase is an enzyme that can transfer a phosphate group from ATP to a tyrosine residue in a protein, through a process called phosphorylation, which is an important mechanism in signal transduction for regulation of enzyme activity. Because kinases are involved in the regulation of a wide variety of normal cellular signal transduction pathways, kinases are thought to play a role in many diseases and disorders. About 50% of the known oncogene products are protein tyrosine kinases (PTKs) and their kinase activity has been shown to lead to cell transformation. Thus, modulation of kinase signaling cascades may be an important way to treat or prevent diseases and disorders.

Inhibitors of various known protein kinases have a variety of therapeutic applications. One promising therapeutic use for protein kinase inhibitors is as anti-cancer agents. 2-(5-(4-(2-morpholinoethoxy)phenyl)pyridin-2-yl)-N-benzylacetamide is a tyrosine kinase inhibitor and capable of modulating a kinase cascade. The free base compound is disclosed in U.S. Pat. No. 7,300,931.

Polymorphism of a compound affects many of the compound's properties, such as solubility, hygroscopicity, chemical reactivity, and stability. Many of the inconsistencies encountered in drug performance can be attributed to polymorphism. Despite the importance of polymorphism, methods of predicting the existence of possible polymorphs of a compound and conditions under which they can be formed are unreliable, and processes for producing polymorphs often fail to generate them consistently and reliably.

Accordingly, there is an urgent need to discover solid form(s) of 2-(5-(4-(2-morpholinoethoxy)phenyl)pyridin-2-yl)-N-benzylacetamide that display desirable physicochemical properties. The present application addresses the need.

SUMMARY

The present application provides solid forms of 2-(5-(4-(2-morpholinoethoxy)phenyl)pyridin-2-yl)-N-benzylacetamide (Compound A) of the following structure:

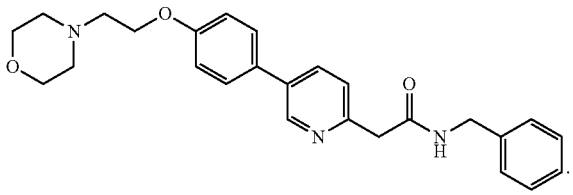 [SMILES: O=C(Cc1ccc(-c2ccc(OCCN3CCOCC3)cc2)cn1)NCc1ccccc1]

In one embodiment, the present application provides crystalline forms of Compound A. In one embodiment, the present application provides polymorphs of Compound A.

In one embodiment, the present application provides a Form A polymorph of Compound A, characterized by an X-ray powder diffraction ("XRPD") pattern comprising peaks at approximately 4.3, 17.0, and 21.1 °2θ using Cu Kα radiation. In one embodiment, Form A is characterized by an XRPD pattern substantially similar to that set forth in FIG. 1, 5, 7, 9, 11, 13, or 18. In one embodiment, Form A appears as birefringent particles as evident by PLM and set forth in FIG. 23.

In one embodiment, the Form A polymorph is characterized by an endothermic event with onset between approximately 124° C. and approximately 135° C., or between approximately 135° C. and approximately 139° C. as measured by DSC. In one embodiment, the Form A polymorph is characterized by endothermic events with onsets between approximately 124° C. and approximately 135° C., and between approximately 135° C. and approximately 139° C. as measured by DSC. In one embodiment, the Form A polymorph is characterized by a TGA or DSC thermogram substantially similar to that set forth in FIG. 12 or 14.

In one embodiment, the present application provides a Form B polymorph of Compound A, characterized by an XRPD pattern comprising peaks at approximately 6.4, 19.3, and 19.9 °2θ using Cu Kα radiation. In one embodiment, the Form B polymorph is characterized by an XRPD pattern substantially similar to that set forth in FIG. 1, 6, 8, 10, 15, or 20. In one embodiment, Form B appears as birefringent particles as evident by PLM and set forth in FIG. 24.

In one embodiment, the Form B polymorph is characterized by an endothermic event with onset between approximately 133° C. and approximately 138° C. as measured by DSC. In one embodiment, the Form B polymorph is characterized by a TGA or DSC thermogram substantially similar to that set forth in FIG. 16.

In one embodiment, the present application provides a Form C polymorph of Compound A, characterized by an XRPD pattern comprising peaks at approximately 7.9, 17.2, and 17.6, and 20.3 °2θ using Cu Kα radiation. In one embodiment, the Form C polymorph is characterized by an XRPD pattern substantially similar to that set forth in FIG. 1 or 2. In one embodiment, Form C appears as birefringent particles as evident by PLM and set forth in FIG. 25.

In one embodiment, the Form C polymorph is characterized by an endothermic event with onset between approximately 136° C. and approximately 140° C. as measured by DSC. In one embodiment, the Form C polymorph is characterized by a TGA or DSC thermogram substantially similar to that set forth in FIG. 3.

In one embodiment, the present application provides an amorphous form of Compound A.

The present application also provides a pharmaceuitcal composition comprising any one of the solid forms of Compound A as described herein (e.g., any of Forms A, B, C, and the amorphous form), and a pharmaceutically acceptable carrier or excipient.

The present application also provides a method of treating or preventing a disease or condition (e.g., a cell proliferative disorder) in which a tyrosine kinase (e.g., an Src tyrosine kinase) plays a role, comprising administering, to a subject in need thereof, a therapeutically effective amount of a composition comprising any one of the solid forms of Compound A as described herein.

The present application also provides a solid form of Compound A as described herein in treating or preventing a disease or condition (e.g., a cell proliferative disorder) in which a tyrosine kinase (e.g., an Src tyrosine kinase) plays a role in a subject in need thereof.

The present application also provides a solid form of Compound A as described herein for use in the manufacture of a medicament for the treatment or prevention of a disease or condition (e.g., a cell proliferative disorder) in which a tyrosine kinase (e.g., an Src tyrosine kinase) plays a role in a subject in need thereof.

The present application also provides use of a solid form of Compound A as described herein in the manufacture of a medicament for the treatment or prevention of a disease or condition (e.g., a cell proliferative disorder) in which a tyrosine kinase (e.g., an Src tyrosine kinase) plays a role in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

Solid Forms

The present application provides solid forms of 2-(5-(4-(2-morpholinoethoxy)phenyl)pyridin-2-yl)-N-benzylacetamide (Compound A) of the following structure:

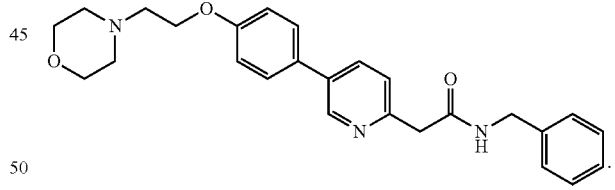

In one embodiment, the present application provides crystalline forms of Compound A. In one embodiment, the present application provides polymorphs of Compound A. In one embodiment, the present application provides a crystalline form of the anhydrate of Compound A. In one embodiment, the present application provides a polymorph of the anhydrate of Compound A.

Form A

In one embodiment, the present application provides a Form A polymorph of Compound A ("Form A") characterized by an X-ray powder diffraction ("XRPD") pattern comprising peaks at approximately 4.3, 17.0, and 21.1 °2θ using Cu Kα radiation. In one embodiment, Form A is characterized by an XRPD pattern comprising peaks at approximately 4.3, 6.4, 8.6, 12.7, 17.0, and 21.1 °2θ using Cu Kα radiation. In one embodiment, Form A is characterized by an XRPD pattern comprising peaks at approximately the positions shown in the table below:

TABLE 1

XRPD peak list for Form A

| Pos. [°2Th.] | Height [cts] | FWHM Left [°2Th.] | d-spacing [Å] | Rel. Int. [%] |
|---|---|---|---|---|
| 4.352568 | 4849.493000 | 0.179088 | 20.30161 | 100.00 |
| 6.429864 | 487.213200 | 0.153504 | 13.74667 | 10.05 |
| 8.564374 | 329.059900 | 0.230256 | 10.32477 | 6.79 |
| 12.680380 | 338.559500 | 0.255840 | 6.98113 | 6.98 |
| 16.559080 | 910.424400 | 0.230256 | 5.35362 | 18.77 |
| 16.850350 | 852.395800 | 0.127920 | 5.26173 | 17.58 |
| 17.029740 | 768.642800 | 0.102336 | 5.20671 | 15.85 |
| 18.536600 | 1555.594000 | 0.281424 | 4.78671 | 32.08 |
| 20.429900 | 810.448200 | 0.204672 | 4.34719 | 16.71 |
| 21.103290 | 1473.067000 | 0.102336 | 4.20997 | 30.38 |
| 21.942280 | 1337.514000 | 0.204672 | 4.05086 | 27.58 |
| 22.601780 | 530.128800 | 0.230256 | 3.93413 | 10.93 |
| 23.231240 | 504.486500 | 0.153504 | 3.82894 | 10.40 |
| 24.490180 | 276.262000 | 0.255840 | 3.63488 | 5.70 |
| 25.648790 | 738.091200 | 0.230256 | 3.47326 | 15.22 |
| 26.623540 | 301.942100 | 0.204672 | 3.34827 | 6.23 |
| 27.685980 | 154.349500 | 0.255840 | 3.22214 | 3.18 |
| 28.357990 | 202.835500 | 0.255840 | 3.14730 | 4.18 |
| 29.880550 | 179.435200 | 0.307008 | 2.99031 | 3.70 |
| 32.441530 | 55.892990 | 0.614016 | 2.75986 | 1.15 |
| 34.144440 | 190.209900 | 0.307008 | 2.62601 | 3.92 |
| 38.562560 | 167.551500 | 0.255840 | 2.33472 | 3.46 |

In one embodiment, Form A is characterized by an XRPD pattern substantially similar to that set forth in FIG. 1, 5, 7, 9, 11, 13, or 18. In one embodiment, Form A is characterized by an XRPD pattern substantially similar to that set forth in FIG. 11.

Figure 23:
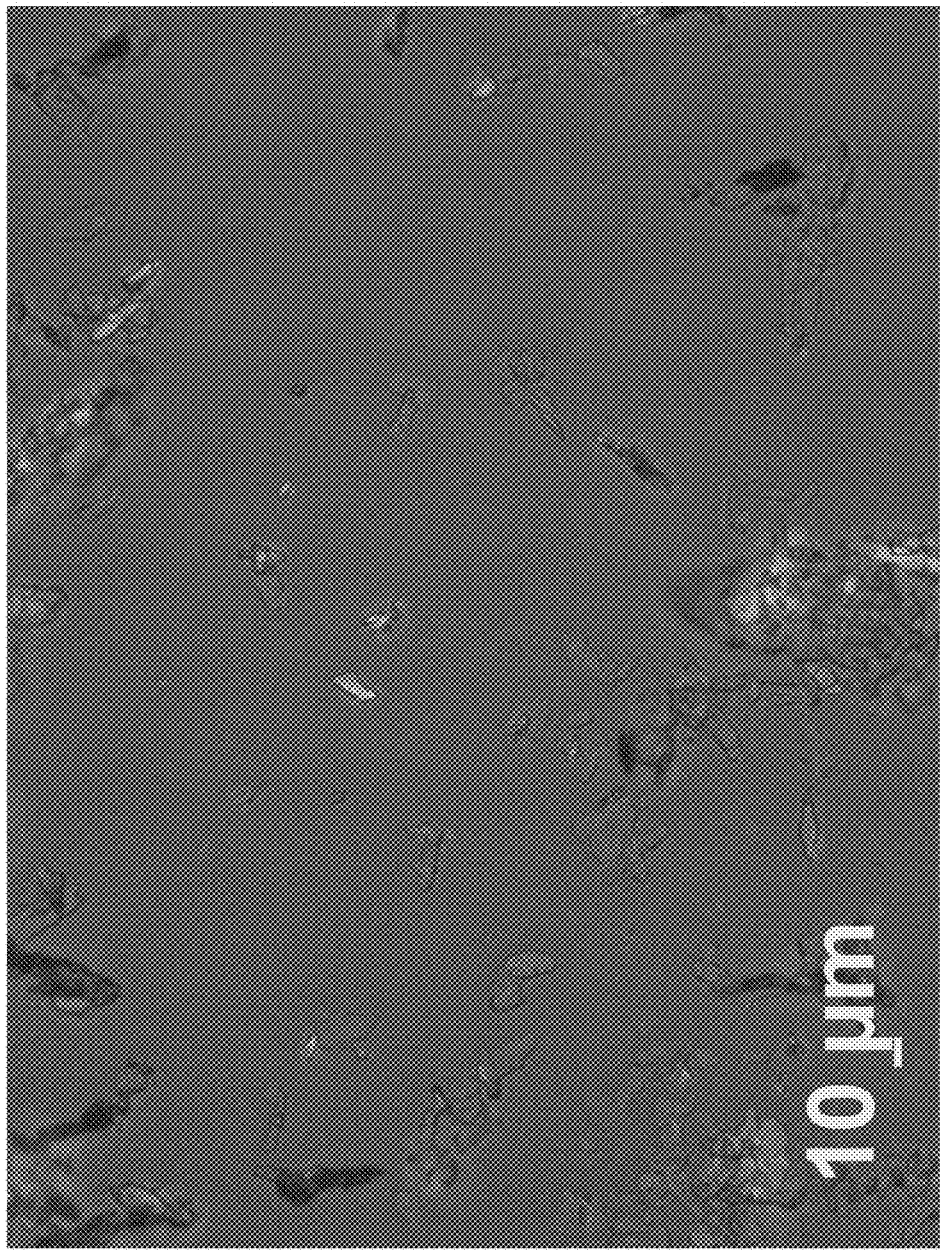
FIG. 23 sets forth a PLM image of Form A.

In one embodiment, Form A appears as birefringent particles as evident by PLM. In one embodiment, Form A appears as set forth in FIG. 23.

In one embodiment, Form A is characterized by an endothermic event with onset at between approximately 124° C. and approximately 135° C., or between approximately 135° C. and approximately 139° C. as measured by DSC. In one embodiment, Form A is characterized by endothermic events with onset at between approximately 124° C. and approximately 135° C., and between approximately 135° C. and approximately 139° C. as measured by DSC. In one embodiment, Form A is characterized by an endothermic event with onset at approximately 124° C. and approximately 135° C. as measured by DSC. In one embodiment, Form A is characterized by an endothermic event with onset at approximately 128° C. as measured by DSC. In one embodiment, Form A is characterized by an endothermic event with onset at approximately 135° C. and approximately 139° C. as measured by DSC. In one embodiment, Form A is characterized by an endothermic event with onset at approximately 138° C. as measured by DSC. In one embodiment, Form A is characterized by endothermic events with onsets at approximately 128° C. and at approximately 138° C. as measured by DSC. In one embodiment, Form A is characterized by a DSC thermogram substantially similar to that set forth in FIG. 12 or 14.

In one embodiment, Form A shows a weight loss of approximately 0.36% between about 33° C. and about 150° C., as measured by TGA.

Figure 17:
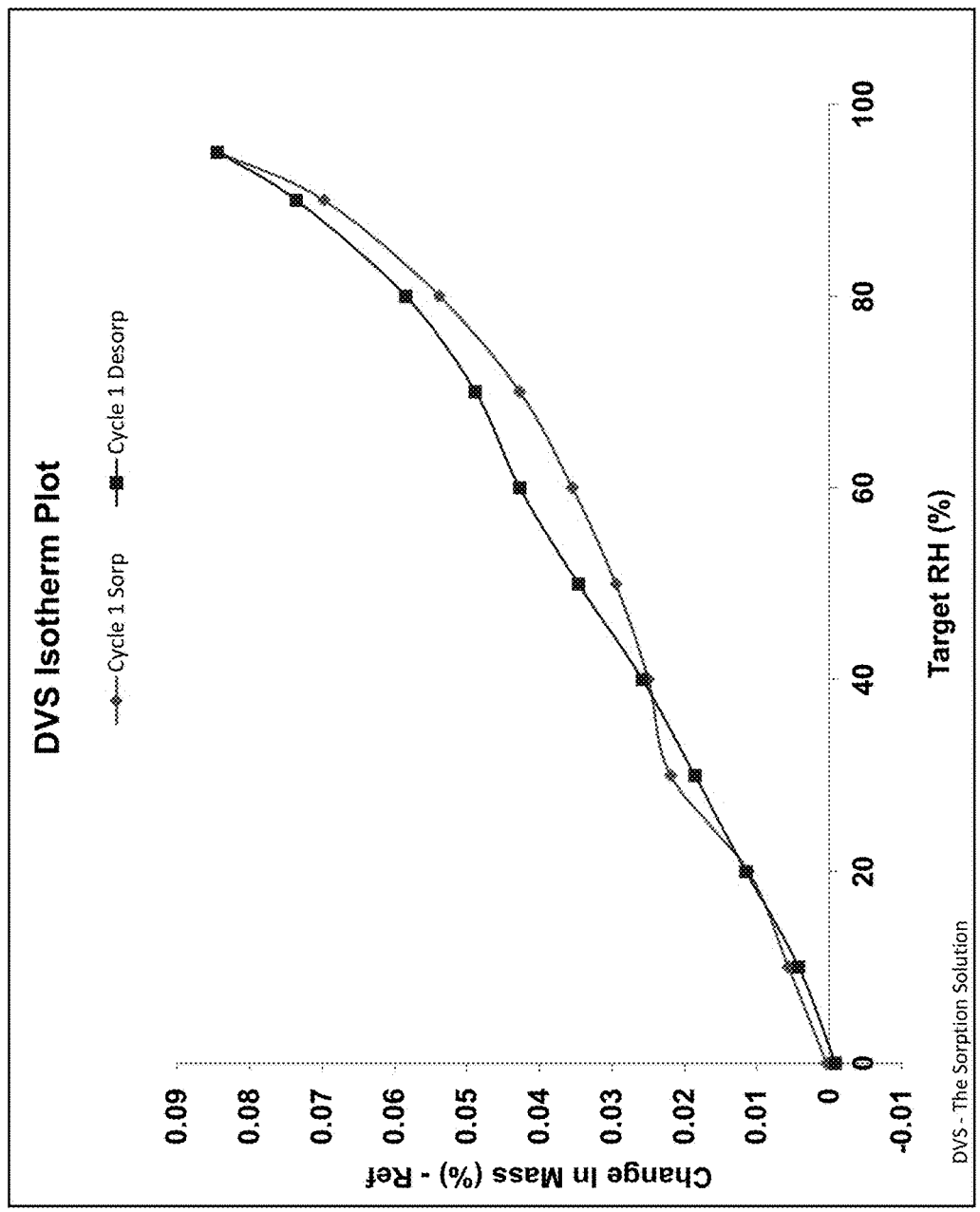
FIG. 17 sets forth a DVS of Form A at 25° C. and RH up to 95%.
Figure 18:
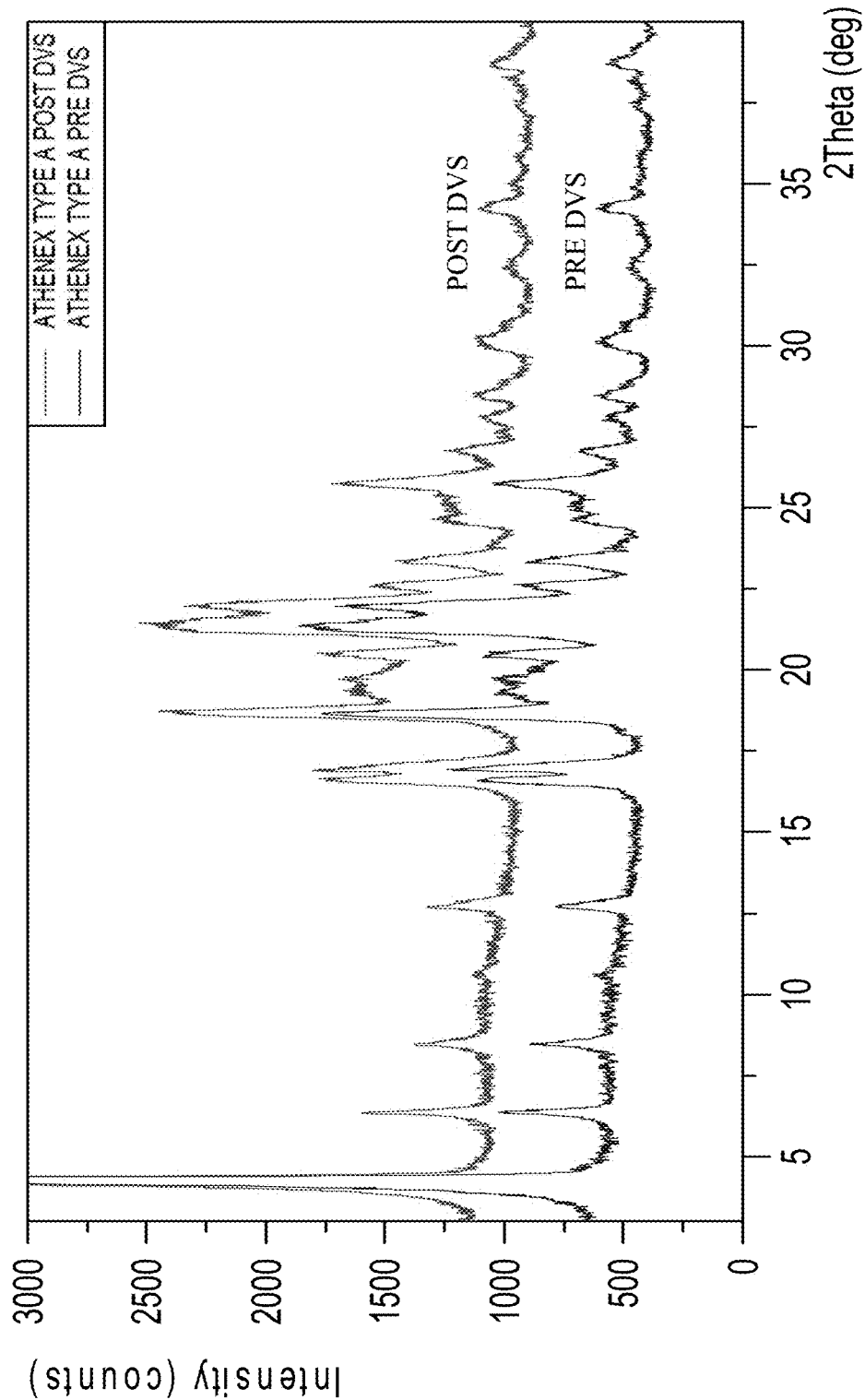
FIG. 18 sets forth an XRPD overlay of Form A pre DVS and Form A post DVS experiment at 25° C. and RH up to 95%.

In one embodiment, Form A is non-hygroscopic. In one embodiment, Form A displays non-hygroscopicity between 0 and 80% RH at between 25° C. and 45° C. (e.g., less than 0.2% w/w water uptake). In one embodiment, Form A displays DVS isotherm at 25° C. and RH up to 95% substantially similar to that set forth in FIG. 17. In one embodiment, the XRPD pattern of Form A does not change after exposure to DVS experiment at 25° C. and RH up to 95%. In one embodiment, the XRPD pattern of Form A post DVS at 25° C. and RH up to 95% is substantially similar to that set forth in FIG. 18.

In one embodiment, Form A is stable under various storage conditions. In one embodiment, Form A is stable at between approximately 20° C. and approximately 250° C., between approximately 20° C. and approximately 200° C., between approximately 20° C. and approximately 180° C., between approximately 20° C. and approximately 160° C., between approximately 20° C. and approximately 140° C., between approximately 20° C. and approximately 120° C., between approximately 20° C. and approximately 100° C., between approximately 20° C. and approximately 80° C., between approximately 20° C. and approximately 60° C., or between approximately 20° C. and approximately 40° C., for at least one week, two weeks, three weeks, one month, two months, three months, four months, six months, or one year. In one embodiment, Form A is stable at between approximately 60% RH and approximately 98% RH (e.g., 75% RH or 96% RH) for at least one week, two weeks, three weeks, one month, two months, three months, four months, six months, or one year. In one embodiment, Form A is stable under ambient conditions for at least one week, two weeks, three weeks, one month, two months, three months, four months, six months, or one year. In one embodiment, Form A is stable under 20-90° C./60%-98% RH for at least one week, two weeks, three weeks, one month, two months, three months, four months, six months, or one year. In one embodiment, Form A is stable under 25° C./60% RH for at least one week, two weeks, three weeks, four weeks, or eight weeks. In one embodiment, Form A is stable under 40° C./75% RH for at least one week, two weeks, three weeks, four weeks, or eight weeks. In one embodiment, Form A is stable under 55° C./75% RH for at least one week, two weeks, three weeks, four weeks, or eight weeks. In one embodiment, HPLC area percent purity (LCAP) results shows no significant decrease in area percent purity for Form A, in the selected conditions, at the given time points over an eight-week study, as shown in the table below:

TABLE 2

HPLC results for Form A

| Material | Condition | Area Percent at 248 nm T0 | Area Percent at 248 nm T1 week | Area Percent at 248 nm T2 week | Area Percent at 248 nm T4 week | Area Percent at 248 nm T8 week |
|---|---|---|---|---|---|---|
| Form A | Ambient | 99.8 | 99.8 | 99.7 | 99.7 | 99.7 |
| | 25° C./60% | 99.8 | 99.8 | 99.8 | 99.8 | 99.8 |
| | 40° C./75% | 99.8 | 99.8 | 99.8 | 99.8 | 99.8 |
| | 55° C./75% | 99.8 | 99.8 | 99.8 | 99.7 | 99.8 |

Figure 26:
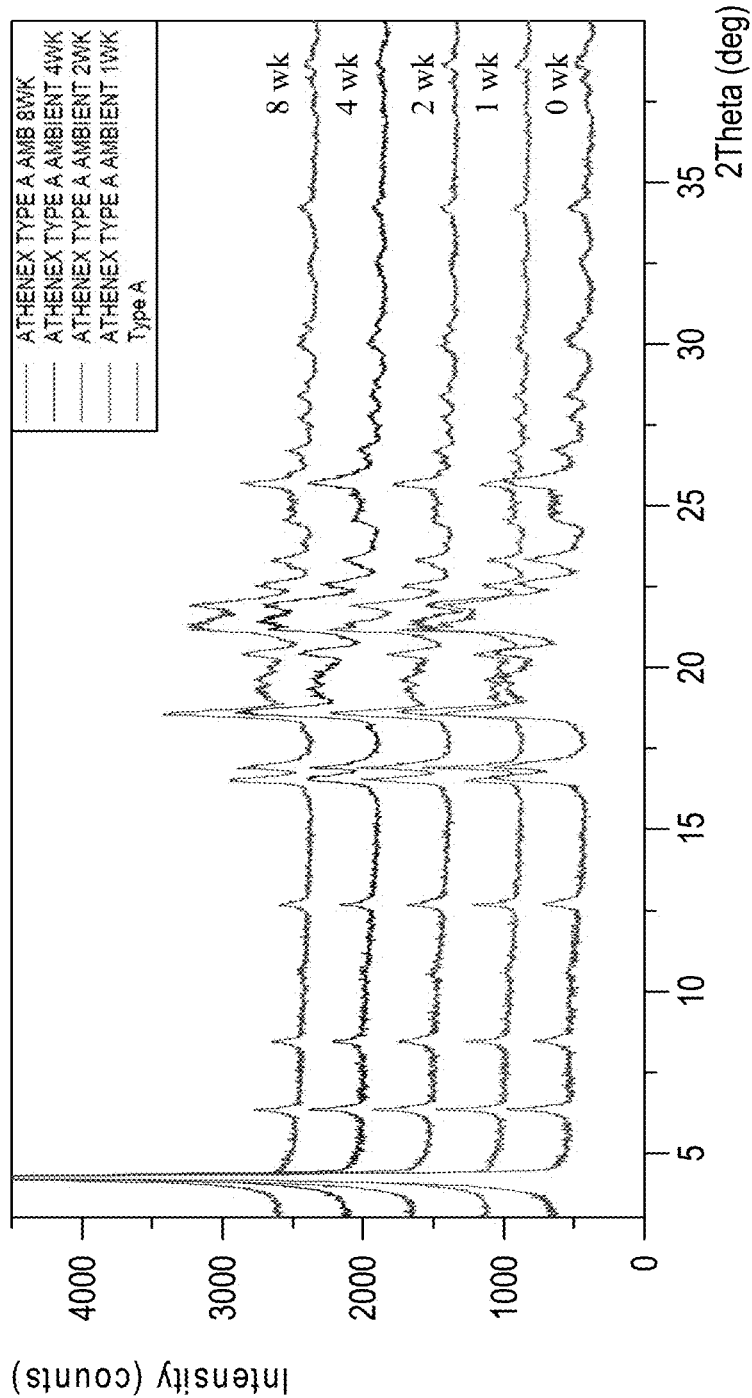
FIG. 26 sets forth an XRPD of Form A in ambient storage condition.
Figure 27:
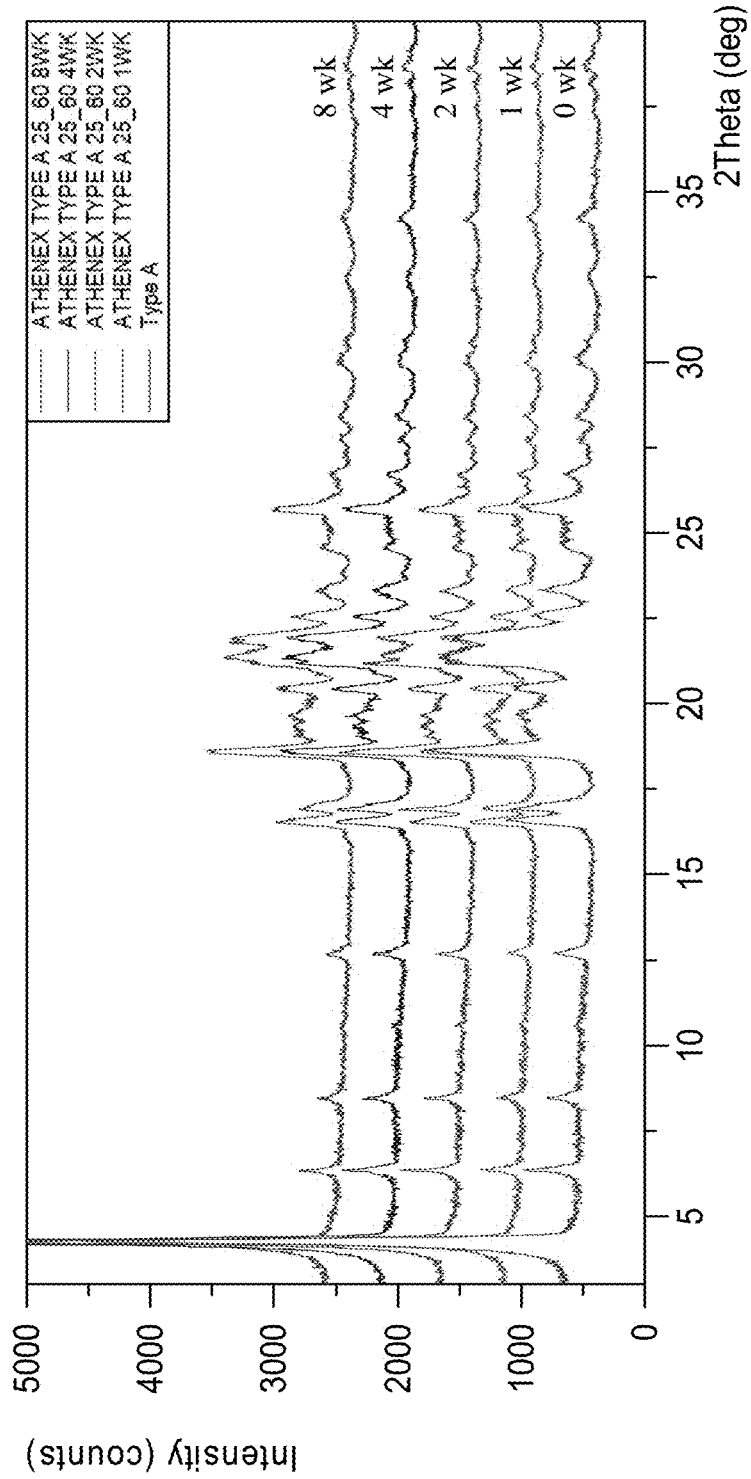
FIG. 27 sets forth an XRPD of Form A in 25° C./60% RH storage condition.
Figure 28:
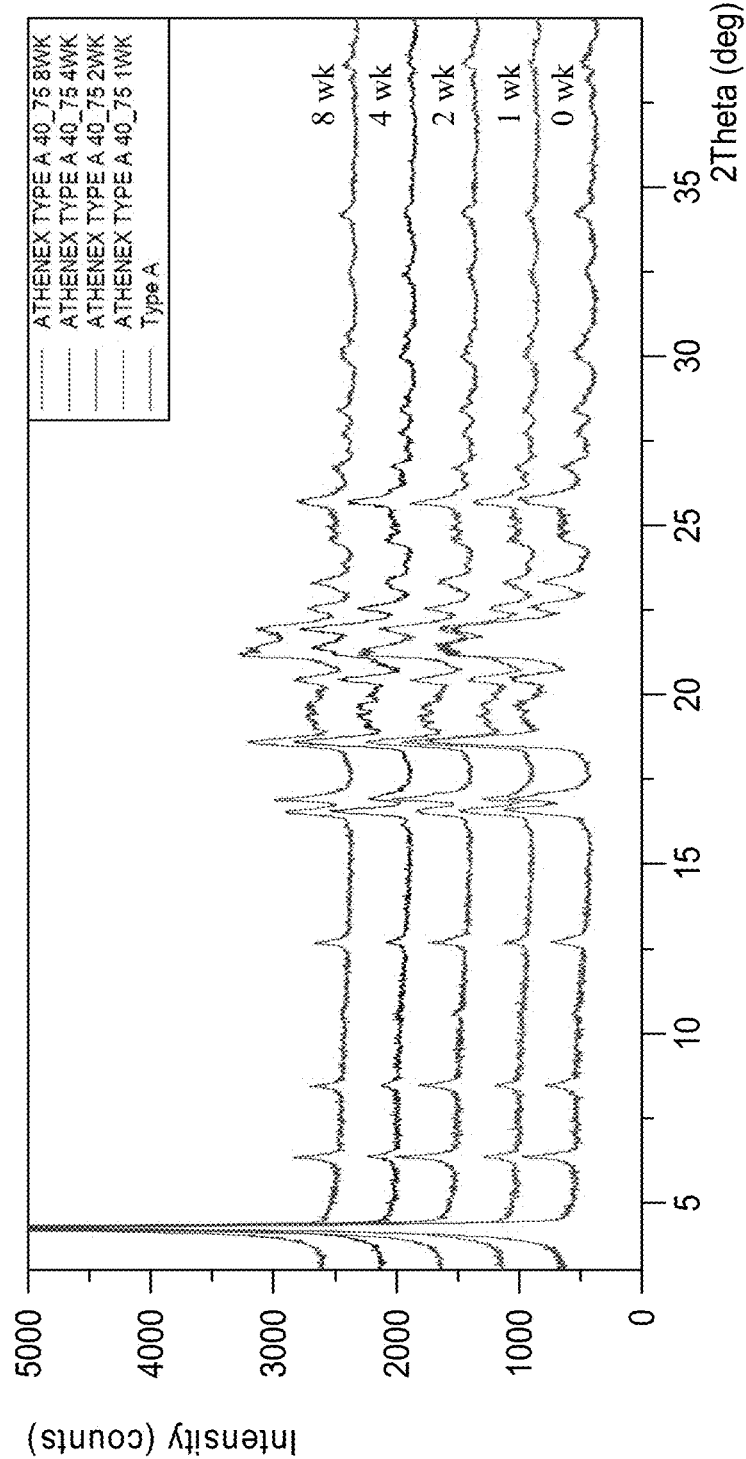
FIG. 28 sets forth an XRPD of Form A in 40° C./75% RH storage condition.
Figure 29:
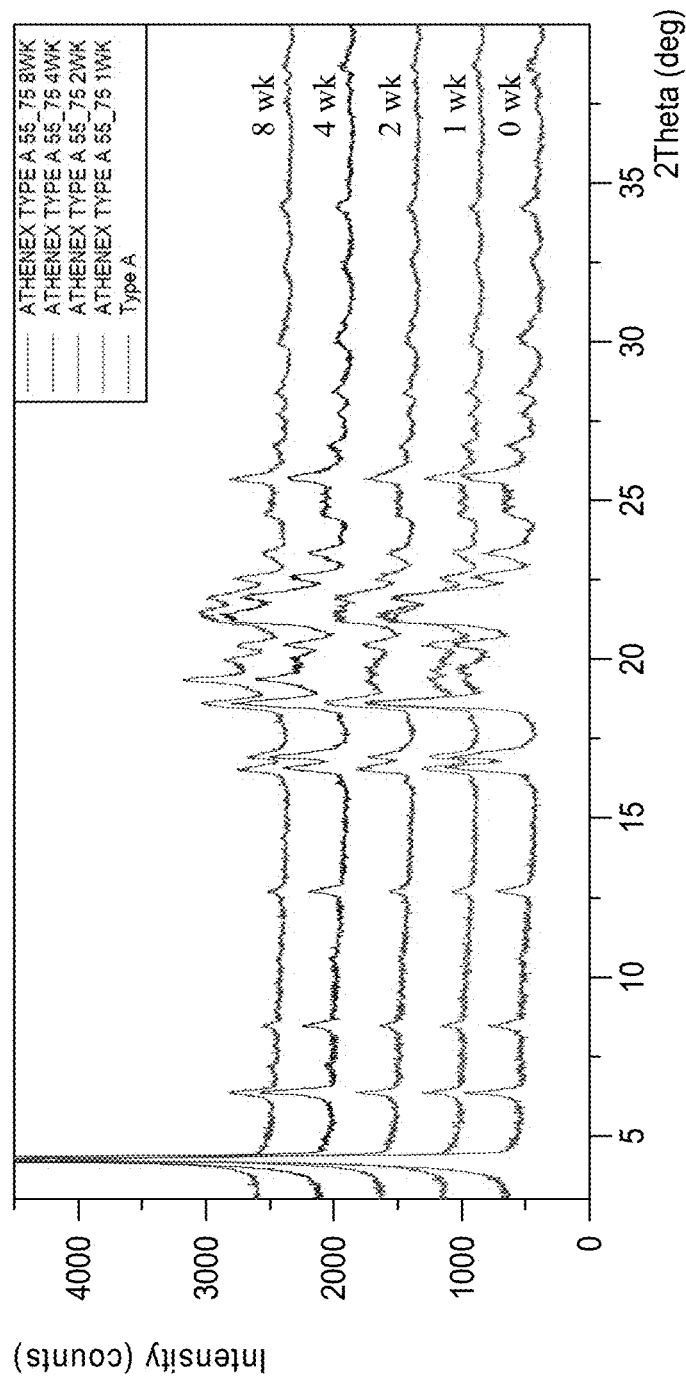
FIG. 29 sets forth an XRPD of Form A in 55° C./75% RH storage condition.

In one embodiment, Form A displays no change in physical form under ambient conditions for at least one week, two weeks, three weeks, four weeks, or eight weeks as set forth in FIG. 26. In one embodiment, Form A displays no change in physical form under 25° C./60% RH for at least one week, two weeks, three weeks, four weeks, or eight weeks as set forth in FIG. 27. In one embodiment, Form A displays no change in physical form under 40° C./75% RH for at least one week, two weeks, three weeks, four weeks, or eight weeks as set forth in FIG. 28. In one embodiment, Form A displays no change in physical form under 55° C./75% RH for at least one week, two weeks, three weeks, four weeks, or eight weeks as set forth in FIG. 29.

In one embodiment, Form A is soluble in an aqueous solution. In one embodiment, Form A is dissolved completely in an aqueous solution (e.g., water) at room temperature (>20 mg/ml). In one embodiment, Form A has a low thermodynamic aqueous solubility (e.g., below 1.5 mg/ml). In one embodiment, Form A forms a gel after being dissolved.

In one embodiment, Form A is an anhydrate.

In one embodiment, Form A is prepared through liquid vapor diffusion. In one embodiment, Form A is prepared by allowing vapor of an anti-solvent to diffuse into a concentrated solution of Compound A in a solvent. In one embodiment, the solvent is methanol or ethanol and the anti-solvent is hexane.

In one embodiment, Form A is prepared through slow cooling of a solution of Compound A.

In one embodiment, Form A is formed by cooling a solution of Compound A in isopropanol. In one embodiment, Form A is formed by slowly cooling a solution of Compound A in a mixture of solvents. In one embodiment, Form A is formed by slowly cooling a solution of Compound A in a mixture of THF and water. In one embodiment, THF and water are mixed at a ratio of about 1:3. In one embodiment, Form A is formed by slowly cooling a solution of Compound A in a mixture of acetone and MTBE. In one embodiment, acetone and MTBE are mixed at a ratio of about 1:3.

In one embodiment, Form A is prepared through anti-solvent addition. In one embodiment, Form A is formed when an anti-solvent is added to a solution of Compound A in chloroform, methanol, acetone, tetrahydrofuran, dioxane, ethanol, 2-Me-THF, ethyl acetate, or dichloromethane. In one embodiment, the anti-solvent is selected from the group consisting of MTBE, water, heptane, isopropanol, MIBK, isopropyl acetate, and toluene. In one embodiment, Form A is formed when chloroform is the solvent and MTBE is the anti-solvent, when methanol is the solvent and water is the anti-solvent, when acetone is the solvent and heptane is the anti-solvent, when tetrahydrofuran is the solvent and MTBE is the anti-solvent, when dioxane is the solvent and water is the anti-solvent, when dioxane is the solvent and MIBK is the anti-solvent, when ethanol is the solvent and isopropyl acetate is the anti-solvent, when 2-Me-THF is the solvent and toluene is the anti-solvent, when ethyl acetate is the solvent and MIBK is the anti-solvent, or when dichloromethane is the solvent and MIBK is the anti-solvent. In one embodiment, a mixture of Form A and Form B is formed when chloroform is the solvent and isopropanol is the anti-solvent.

Form B

In one embodiment, the present application provides a Form B polymorph of Compound A ("Form B") characterized by an XRPD pattern comprising peaks at approximately 6.4, 19.3, and 19.9 °2θ using Cu Kα radiation. In one embodiment, Form B is characterized by an XRPD pattern comprising peaks at approximately 6.4, 7.2, 19.3, 19.9, 21.6, 22.1, and 22.6 °2θ using Cu Kα radiation. In one embodiment, Form B is characterized by an XRPD pattern comprising peaks at approximately the positions shown in the table below:

TABLE 3

XRPD peak list for Form B

| Pos. [°2Th.] | Height [cts] | FWHM Left [°2Th.] | d-spacing [Å] | Rel. Int. [%] |
|---|---|---|---|---|
| 6.396556 | 1023.858000 | 0.204672 | 13.81818 | 32.87 |
| 7.223744 | 358.135900 | 0.307008 | 12.23762 | 11.50 |
| 11.259270 | 100.557900 | 0.307008 | 7.85887 | 3.23 |
| 12.417860 | 89.051790 | 0.307008 | 7.12812 | 2.86 |
| 14.451710 | 107.891800 | 0.307008 | 6.12921 | 3.46 |
| 16.312250 | 170.214900 | 0.307008 | 5.43407 | 5.46 |
| 17.993430 | 275.519000 | 0.307008 | 4.92996 | 8.84 |
| 19.252160 | 3061.096000 | 0.332592 | 4.61038 | 98.27 |
| 19.915580 | 3115.026000 | 0.307008 | 4.45828 | 100.00 |
| 21.624070 | 804.428900 | 0.332592 | 4.10974 | 25.82 |
| 22.114130 | 1150.632000 | 0.281424 | 4.01976 | 36.94 |
| 22.595820 | 1445.826000 | 0.230256 | 3.93515 | 46.41 |
| 24.181720 | 500.959000 | 0.307008 | 3.68055 | 16.08 |
| 25.668170 | 278.847300 | 0.307008 | 3.47068 | 8.95 |
| 28.492680 | 203.141000 | 0.409344 | 3.13273 | 6.52 |
| 32.181410 | 114.869600 | 0.358176 | 2.78157 | 3.69 |
| 34.483340 | 37.820360 | 0.614016 | 2.60098 | 1.21 |
| 37.646040 | 115.043200 | 0.409344 | 2.38942 | 3.69 |

In one embodiment, Form B is characterized by an XRPD pattern substantially similar to that set forth in FIG. 1, 6, 8, 10, 15, or 20. In one embodiment, Form B is characterized by an XRPD pattern substantially similar to that set forth in FIG. 15.

Figure 24:
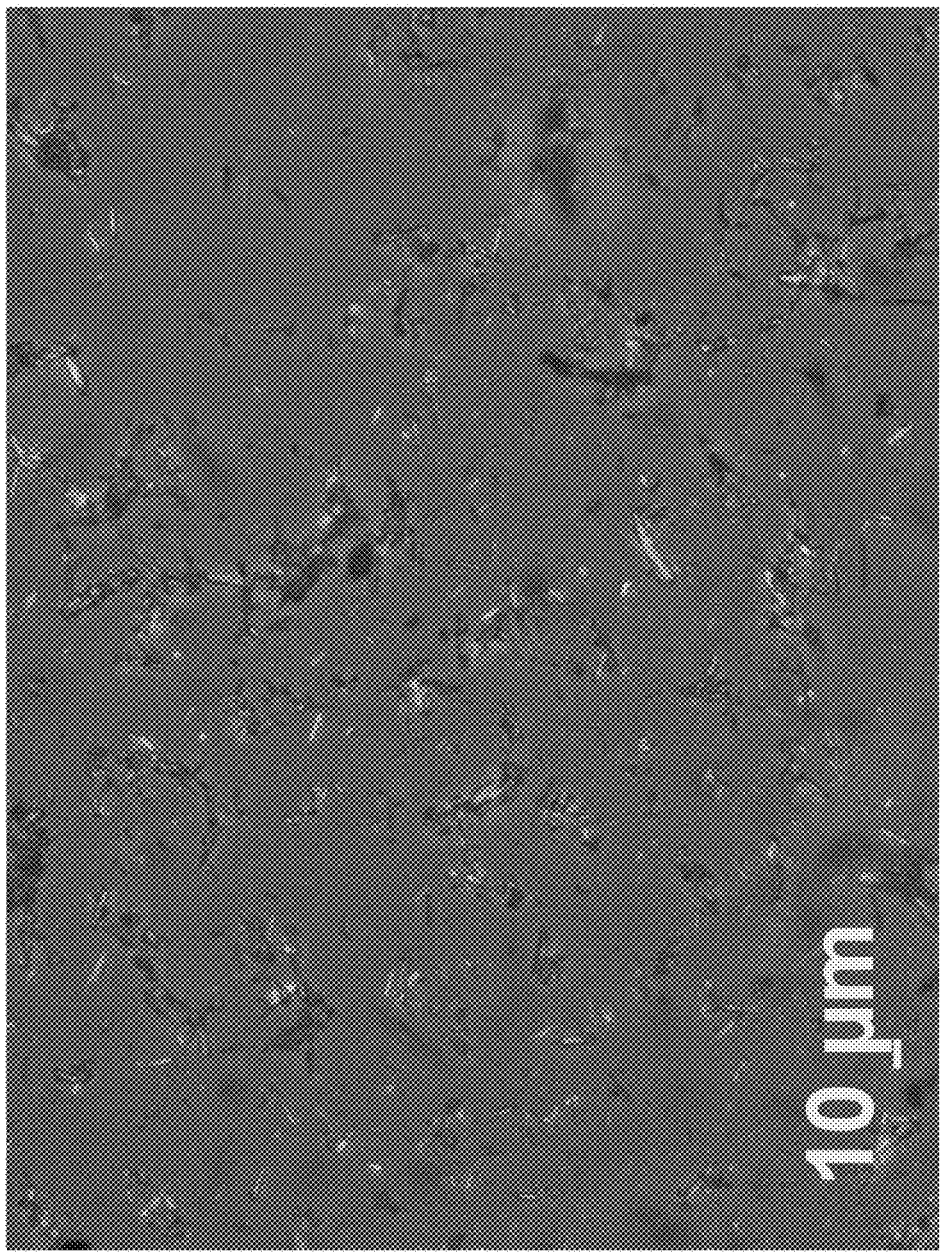
FIG. 24 sets forth a PLM image of Form B.

In one embodiment, Form B appears as birefringent particles as evident by PLM. In one embodiment, Form A appears as set forth in FIG. 24.

In one embodiment, Form B is characterized by an endothermic event with onset at between approximately 133° C. and approximately 138° C. as measured by DSC. In one embodiment, Form B is characterized by an endothermic event with onset at approximately 136° C. as measured by DSC. In one embodiment, Form B is characterized by a DSC thermogram substantially similar to that set forth in FIG. 16.

In one embodiment, Form B shows a weight loss of approximately 0.20% between about 33° C. and about 150° C., as measured by TGA.

Figure 19:
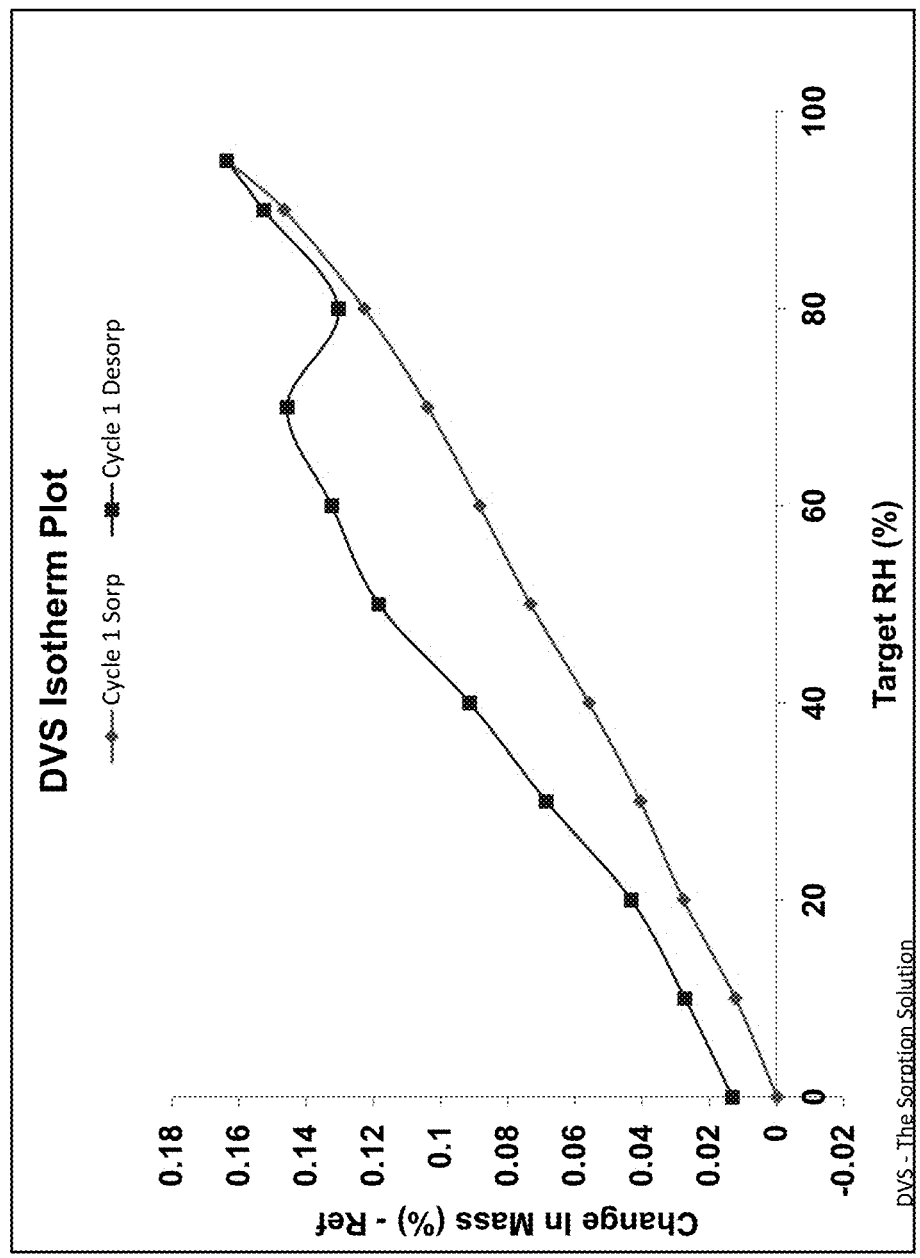
FIG. 19 sets forth a DVS of Form B at 25° C. and RH up to 95%.
Figure 20:
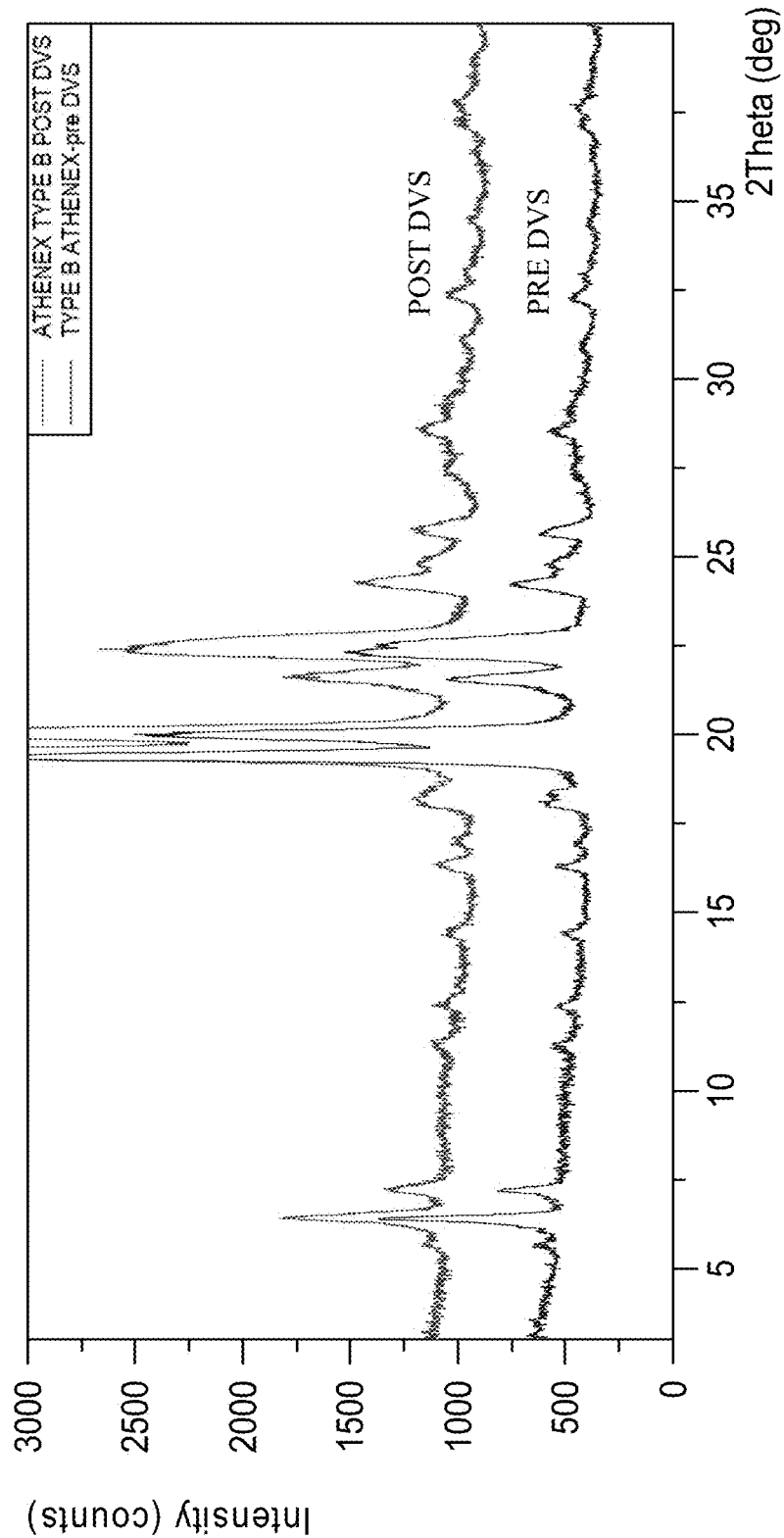
FIG. 20 sets forth an XRPD overlay of Form B pre DVS and Form B post DVS experiment at 25° C. and RH up to 95%.

In one embodiment, Form B is non-hygroscopic. In one embodiment, Form B displays non-hygroscopicity between 0 and 80% RH at between 25° C. and 45° C. (e.g., less than 0.2% w/w water uptake). In one embodiment, Form B displays DVS isotherm at 25° C. and RH up to 95% substantially similar to that set forth in FIG. 19. In one embodiment, the XRPD pattern of Form B does not change after exposure to DVS experiment at 25° C. and RH up to 95%. In one embodiment, the XRPD pattern of Form B post DVS at 25° C. and RH up to 95% is substantially similar to that set forth in FIG. 20.

In one embodiment, Form B is stable under various storage conditions. In one embodiment, Form B is stable at between approximately 20° C. and approximately 250° C., between approximately 20° C. and approximately 200° C., between approximately 20° C. and approximately 180° C., between approximately 20° C. and approximately 160° C., between approximately 20° C. and approximately 140° C., between approximately 20° C. and approximately 120° C., between approximately 20° C. and approximately 100° C., between approximately 20° C. and approximately 80° C., between approximately 20° C. and approximately 60° C., or between approximately 20° C. and approximately 40° C., for at least one week, two weeks, three weeks, one month, two months, three months, four months, six months, or one year. In one embodiment, Form B is stable at between approximately 60% RH and approximately 98% RH (e.g., 75% RH or 96% RH) for at least one week, two weeks, three weeks, one month, two months, three months, four months, six months, or one year. In one embodiment, Form B is stable under ambient conditions for at least one week, two weeks, three weeks, one month, two months, three months, four months, six months, or one year. In one embodiment, Form B is stable under 20-90° C./60%-98% RH for at least one week, two weeks, three weeks, one month, two months, three months, four months, six months, or one year. In one embodiment, Form B is stable under 25° C./60% RH for at least one week, two weeks, three weeks, four weeks, or eight weeks. In one embodiment, Form B is stable under 40° C./75% RH for at least one week, two weeks, three weeks, four weeks, or eight weeks. In one embodiment, Form B is stable under 55° C./75% RH for at least one week, two weeks, three weeks, four weeks, or eight weeks. In one embodiment, HPLC area percent purity (LCAP) results shows no significant decrease in area percent purity for Form B, in the selected conditions, at the given time points over eight week study, as shown in the table below:

In one embodiment, Form B is an anhydrate.

In one embodiment, Form B is prepared by slurrying Compound A in a solvent. In one embodiment, Form B is prepared by slurrying Compound A in chloroform. In one embodiment, the slurrying is conducted at room temperature. In one embodiment, the slurrying is conducted with continuous agitation. In one embodiment, slurrying Compound A in chloroform generates a mixture of Form B and Form C.

In one embodiment, Form B is prepared through liquid vapor diffusion. In one embodiment, Form B is prepared by allowing vapor of an anti-solvent to diffuse into a concentrated solution of Compound A in a solvent. In one embodiment, a solution of Compound A is converted to Form B when the solvent is methanol and the anti-solvent is MTBE. In one embodiment, the solvent is chloroform and the anti-solvent is MTBE.

In one embodiment, Form B is prepared through slow cooling of a solution of Compound A.

In one embodiment, Form B is formed by cooling a solution of Compound A in acetone, isopropyl acetate, 2-Me-THF, ethyl acetate, or acetonitrile. In one embodiment, Form B is formed by slowly cooling a solution of Compound A in a mixture of solvents. In one embodiment, Form B is formed by slowly cooling a solution of Compound A in a mixture of chloroform and heptane. In one embodiment, chloroform and heptane are mixed at a ratio of about 1:3. In one embodiment, Form B is formed by slowly cooling a solution of Compound A in a mixture of dioxane and isopropyl acetate. In one embodiment, dioxane and isopropyl acetate are mixed at a ratio of about 1:3.

In one embodiment, Form B is prepared through anti-solvent addition. In one embodiment, Form B is formed when an anti-solvent is added to a solution of Compound A

TABLE 4

HPLC results for Form B

| Material | Condition | Area Percent at 248 nm T0 | Area Percent at 248 nm T1 week | Area Percent at 248 nm T2 week | Area Percent at 248 nm T4 week | Area Percent at 248 nm T8 week |
|---|---|---|---|---|---|---|
| Form B | Ambient | 99.8 | 99.8 | 99.7 | 99.8 | 99.8 |
| | 25° C./60% | 99.8 | 99.8 | 99.7 | 99.8 | 99.8 |
| | 40° C./75% | 99.8 | 99.8 | 99.8 | 99.7 | 99.8 |
| | 55° C./75% | 99.8 | 99.8 | 99.7 | 99.7 | 99.7 |

Figure 30:
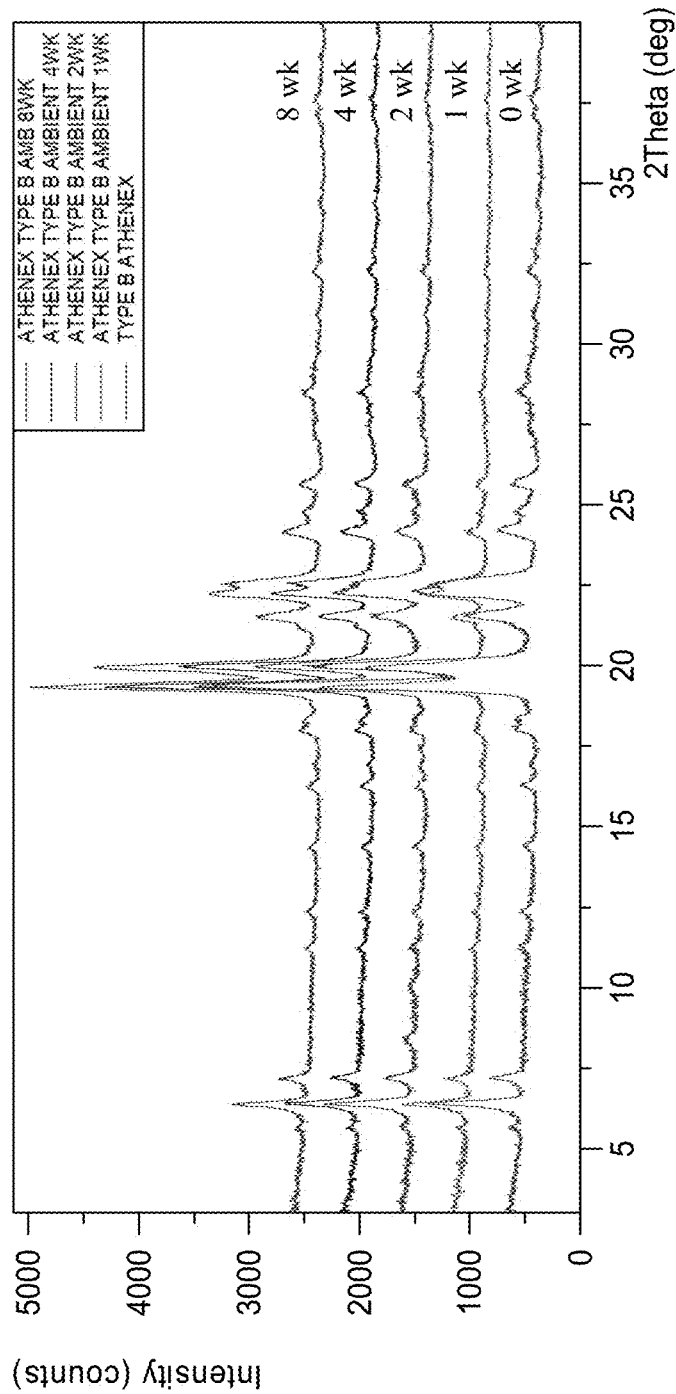
FIG. 30 sets forth an XRPD of Form B in ambient storage condition.
Figure 31:
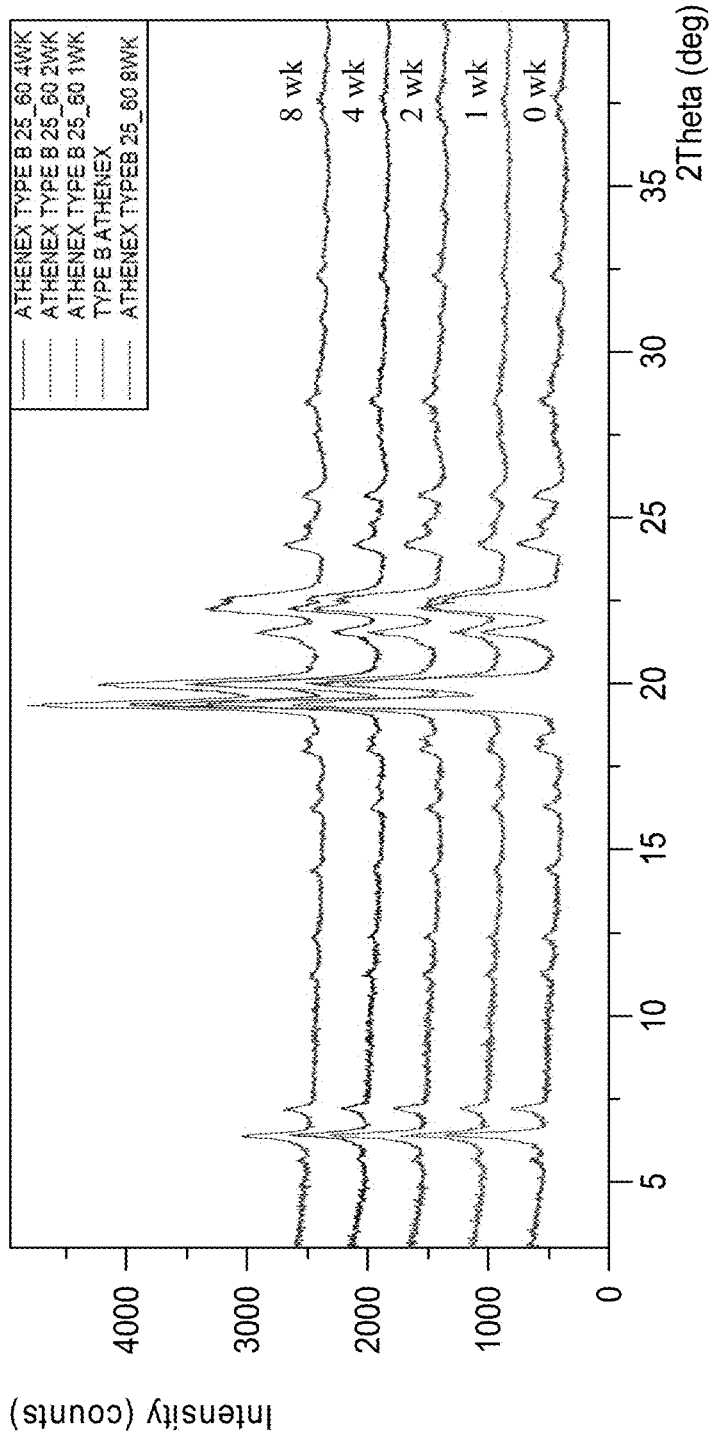
FIG. 31 sets forth an XRPD of Form B in 25° C./60% RH storage condition.
Figure 32:
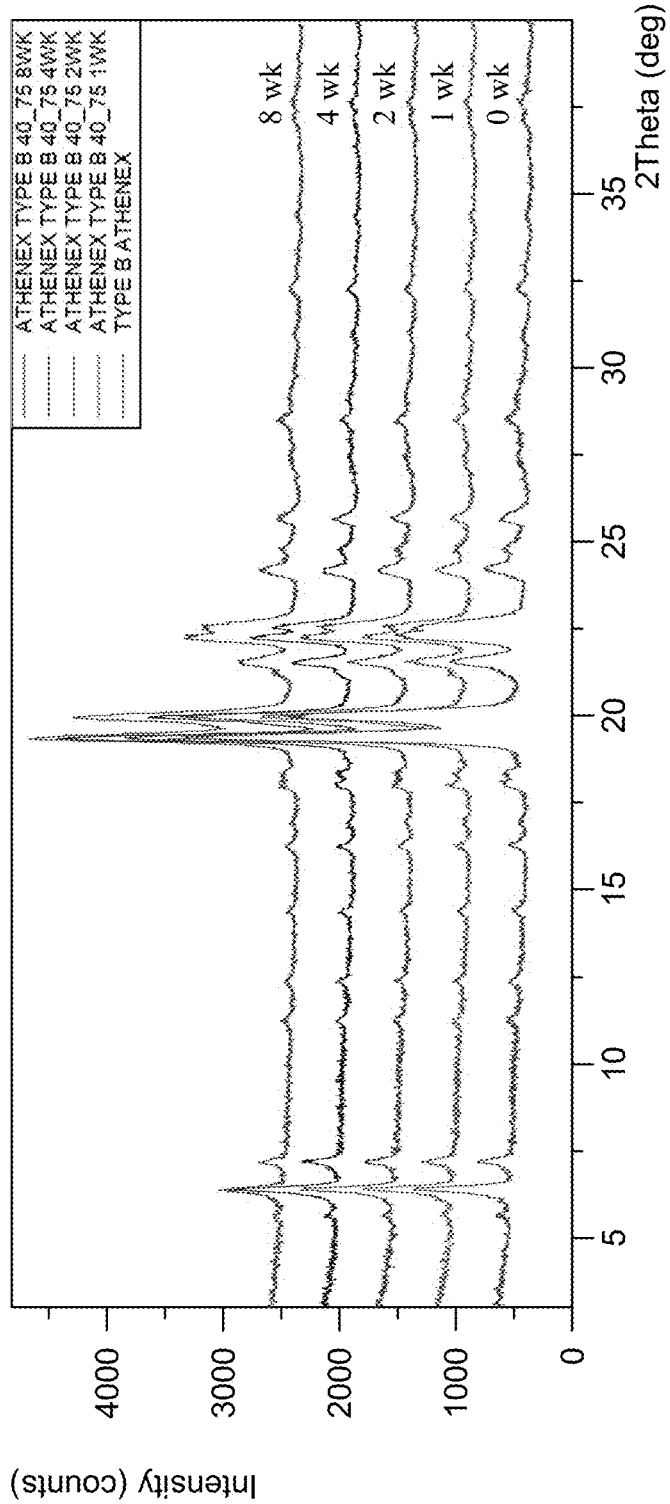
FIG. 32 sets forth an XRPD of Form B in 40° C./75% RH storage condition.
Figure 33:
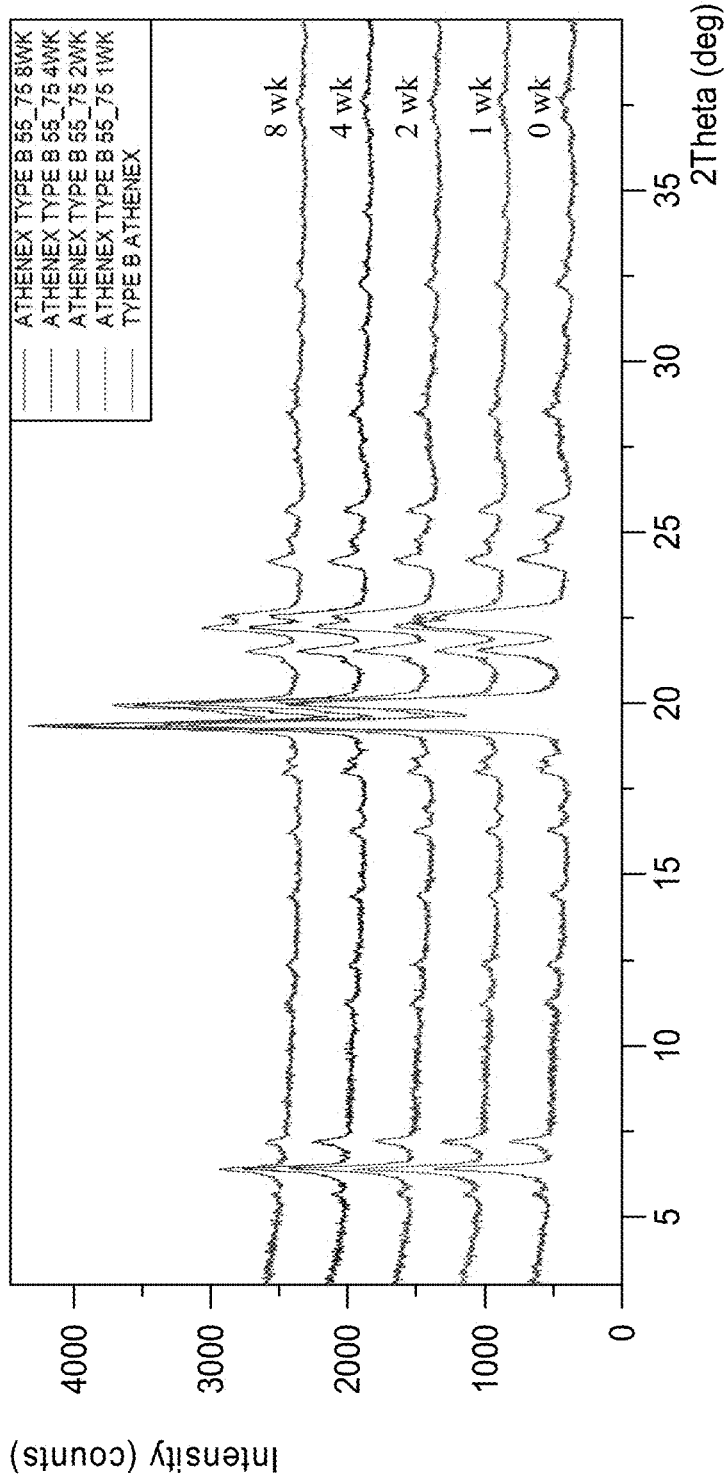
FIG. 33 sets forth an XRPD of Form B in 55° C./75% RH storage condition.

In one embodiment, Form B displays no change in physical form under ambient conditions for at least one week, two weeks, three weeks, four weeks, or eight weeks as set forth in FIG. 30. In one embodiment, Form B displays no change in physical form under 25° C./60% RH for at least one week, two weeks, three weeks, four weeks, or eight weeks as set forth in FIG. 31. In one embodiment, Form B displays no change in physical form under 40° C./75% RH for at least one week, two weeks, three weeks, four weeks, or eight weeks as set forth in FIG. 32. In one embodiment, Form B displays no change in physical form under 55° C./75% RH for at least one week, two weeks, three weeks, four weeks, or eight weeks as set forth in FIG. 33.

In one embodiment, Form B is soluble in an aqueous solution. In one embodiment, Form B is dissolved completely in an aqueous solution (e.g., water) at room temperature (>20 mg/ml). In one embodiment, Form B has a low thermodynamic aqueous solubility (e.g., below 1.5 mg/ml). In one embodiment, Form B forms a gel after being dissolved.

in chloroform, methanol, acetone, or acetonitrile. In one embodiment, the anti-solvent is selected from the group consisting of isopropyl acetate, toluene, and isopropanol. In one embodiment, Form B is formed when methanol is the solvent and isopropyl acetate is the anti-solvent, when acetone is the solvent and toluene is the anti-solvent, or when acetonitrile is the solvent and isopropanol is the anti-solvent. In one embodiment, a mixture of Form A and Form B is formed when the chloroform is the solvent and isopropanol is the anti-solvent.

Form C

In one embodiment, the present application provides a Form C polymorph of Compound A ("Form C") characterized by an XRPD pattern comprising peaks at approximately 7.9, 17.2, and 17.6 °2θ using Cu Kα radiation. In one embodiment, Form C is characterized by an XRPD pattern comprising peaks at approximately 5.8, 7.9, 8.7, 17.2, and 17.6 °2θ using Cu Kα radiation. In one embodiment, Form C is characterized by an XRPD pattern comprising peaks at approximately the positions shown in the table below:

TABLE 5

XRPD peak list for Form C

| Pos. [°2Th.] | Height [cts] | FWHM Left [°2Th.] | d-spacing [Å] | Rel. Int. [%] |
|---|---|---|---|---|
| 5.841336 | 964.614800 | 0.204672 | 15.13030 | 16.42 |
| 6.025648 | 653.891900 | 0.127920 | 14.66790 | 11.13 |
| 7.933055 | 1682.623000 | 0.281424 | 11.14495 | 28.64 |
| 8.709872 | 748.455500 | 0.127920 | 10.15262 | 12.74 |
| 11.544940 | 348.086300 | 0.255840 | 7.66505 | 5.92 |
| 12.455120 | 322.348400 | 0.409344 | 7.10688 | 5.49 |
| 13.685470 | 248.341700 | 0.307008 | 6.47060 | 4.23 |
| 15.640940 | 103.700100 | 0.255840 | 5.66576 | 1.76 |
| 17.179580 | 1067.798000 | 0.127920 | 5.16163 | 18.17 |
| 17.574450 | 4391.382000 | 0.102336 | 5.04654 | 74.73 |
| 17.763970 | 5875.947000 | 0.204672 | 4.99312 | 100.00 |
| 18.796350 | 980.068000 | 0.255840 | 4.72114 | 16.68 |
| 19.300230 | 1446.590000 | 0.307008 | 4.59901 | 24.62 |
| 20.335720 | 2343.389000 | 0.307008 | 4.36711 | 39.88 |
| 21.715320 | 848.299000 | 0.179088 | 4.09268 | 14.44 |
| 22.202770 | 710.811600 | 0.153504 | 4.00392 | 12.10 |
| 22.376490 | 718.672400 | 0.102336 | 3.97323 | 12.23 |
| 22.665620 | 609.531300 | 0.230256 | 3.92319 | 10.37 |
| 23.681750 | 929.568700 | 0.153504 | 3.75711 | 15.82 |
| 24.133420 | 347.999900 | 0.255840 | 3.68780 | 5.92 |
| 24.658910 | 981.961300 | 0.307008 | 3.61039 | 16.71 |
| 25.630530 | 1590.663000 | 0.332592 | 3.47569 | 27.07 |
| 27.114160 | 174.151800 | 0.358176 | 3.28878 | 2.96 |
| 27.855950 | 376.955800 | 0.358176 | 3.20287 | 6.42 |
| 28.815190 | 450.055900 | 0.153504 | 3.09839 | 7.66 |
| 30.732120 | 94.724980 | 0.255840 | 2.90936 | 1.61 |
| 32.065250 | 121.770900 | 0.255840 | 2.79138 | 2.07 |
| 33.159240 | 145.564800 | 0.307008 | 2.70175 | 2.48 |
| 34.366360 | 69.459230 | 0.307008 | 2.60956 | 1.18 |
| 36.179660 | 145.473900 | 0.255840 | 2.48283 | 2.48 |
| 36.847060 | 222.320100 | 0.307008 | 2.43938 | 3.78 |
| 38.090690 | 91.491560 | 0.307008 | 2.36254 | 1.56 |

In one embodiment, Form C is characterized by an XRPD pattern substantially similar to that set forth in FIG. 1, 6, 8, 10, or 15. In one embodiment, Form C is characterized by an XRPD pattern substantially similar to that set forth in FIG. 1 or FIG. 2.

Figure 25:
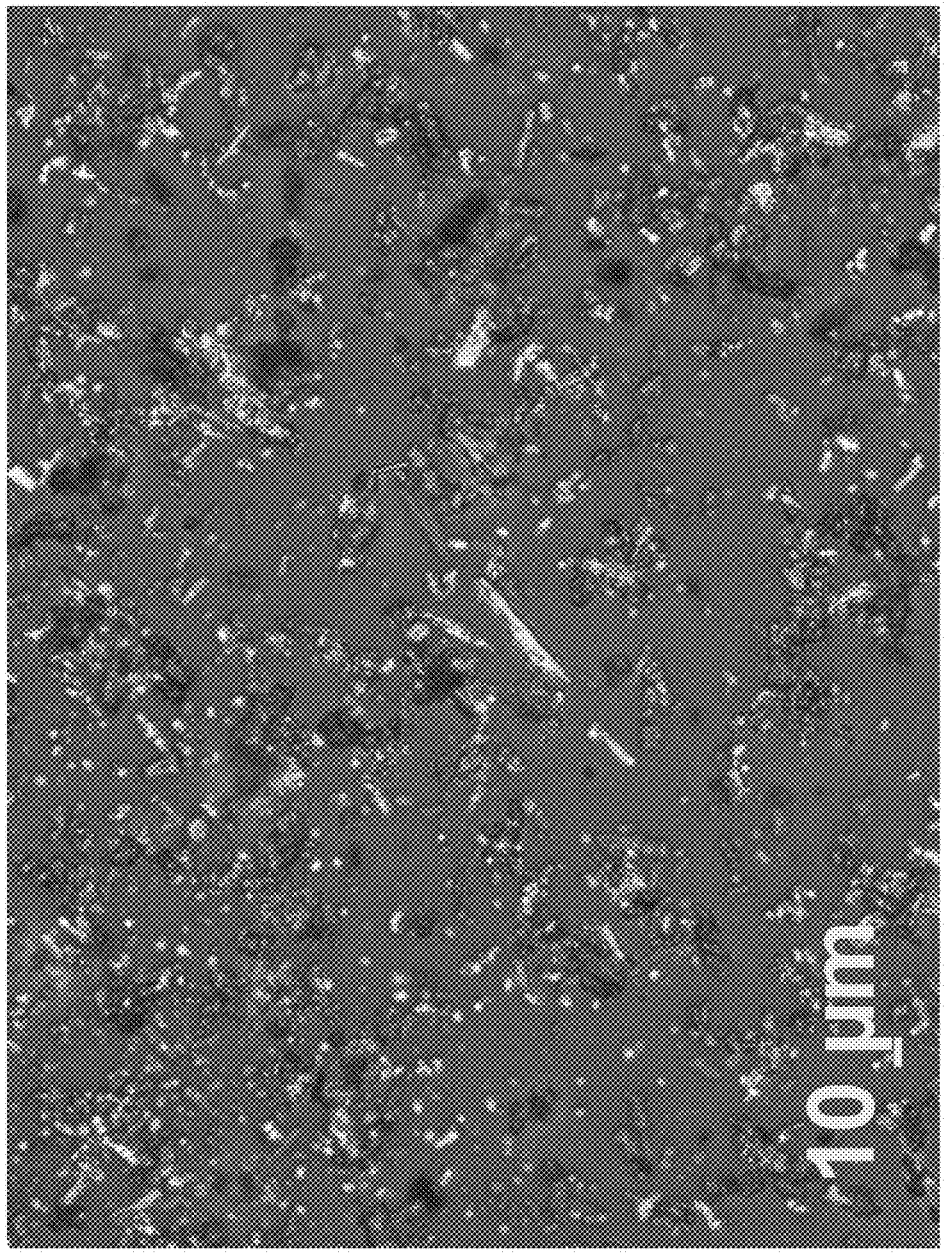
FIG. 25 sets forth a PLM image of Form C.

In one embodiment, Form C appears as birefringent particles as evident by PLM. In one embodiment, Form A appears as set forth in FIG. 25.

In one embodiment, Form C is characterized by an endothermic event with onset at between approximately 136° C. and approximately 140° C. as measured by DSC. In one embodiment, Form C is characterized by an endothermic event with onset at approximately 136° C. as measured by DSC. In one embodiment, Form C is characterized by a DSC thermogram substantially similar to that set forth in FIG. 3.

In one embodiment, Form C shows a weight loss of approximately 0.18% between about 33° C. and about 150° C., as measured by TGA.

Figure 21:
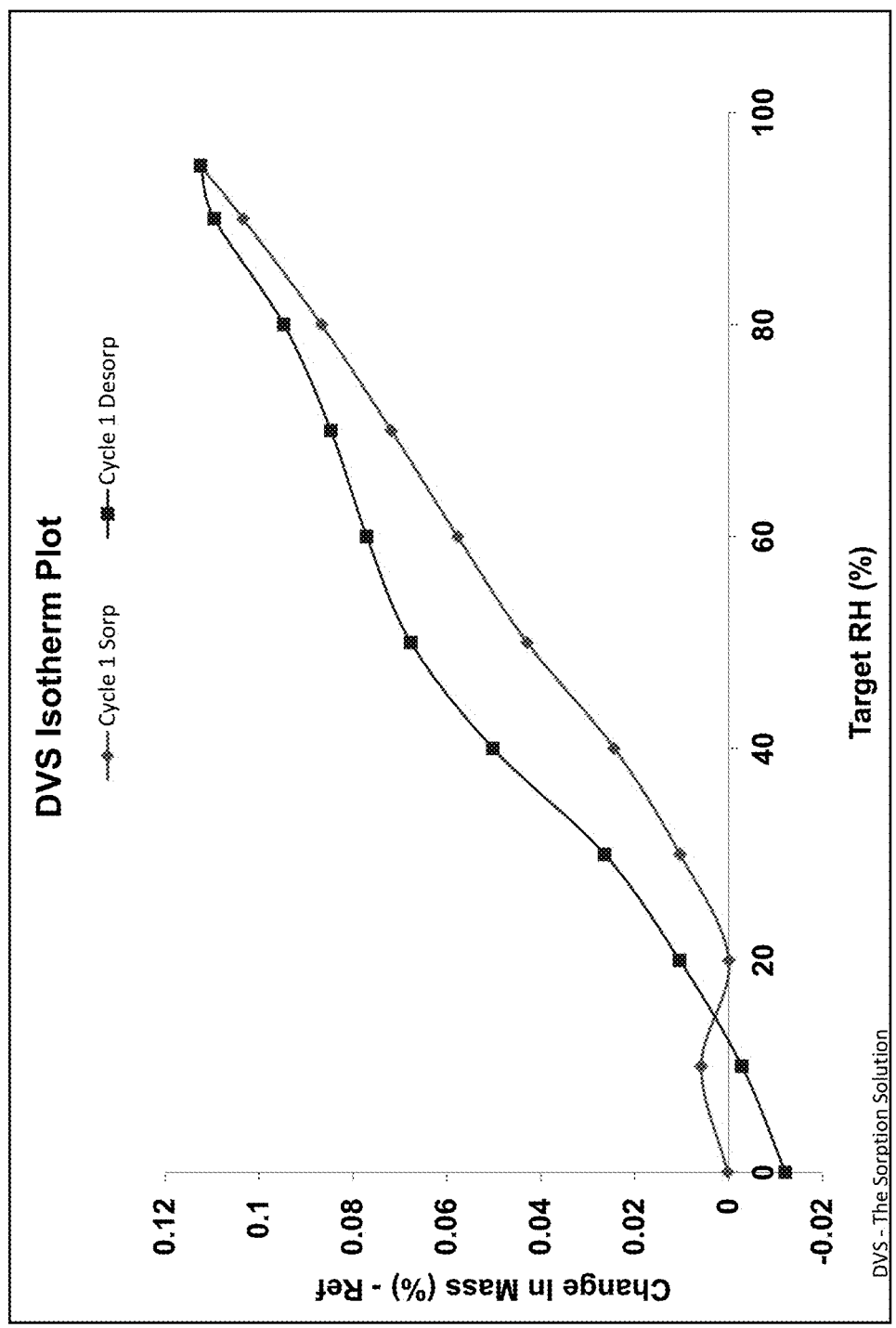
FIG. 21 sets forth a DVS of Form C at 25° C. and RH up to 95%.
Figure 22:
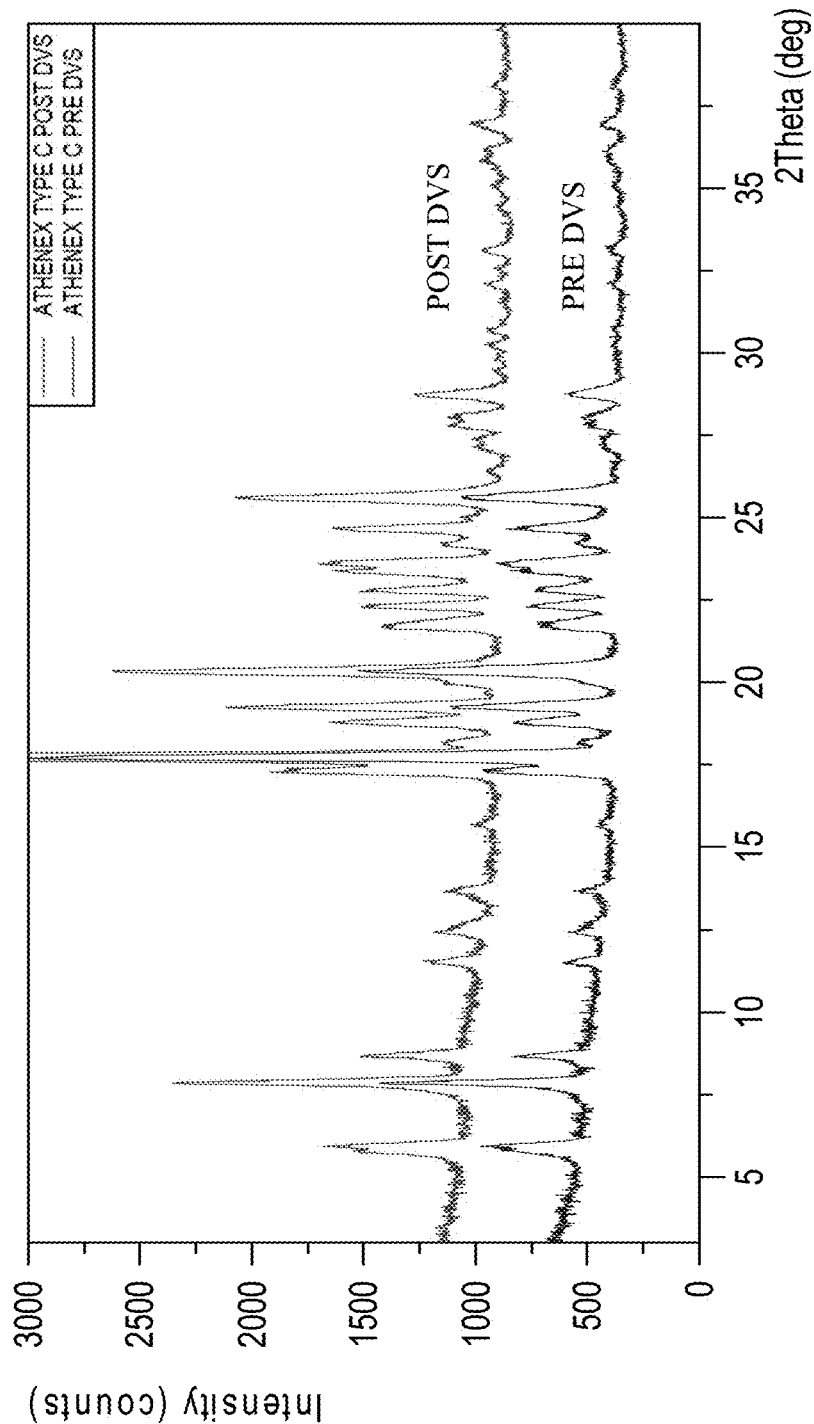
FIG. 22 sets forth an XRPD overlay of Form C pre DVS and Form B post DVS experiment at 25° C. and RH up to 95%.

In one embodiment, Form C is non-hygroscopic. In one embodiment, Form C displays non-hygroscopicity between 0 and 80% RH at between 25° C. and 45° C. (e.g., less than 0.2% w/w water uptake). In one embodiment, Form C displays DVS isotherm at 25° C. and RH up to 95% substantially similar to that set forth in FIG. 21. In one embodiment, the XRPD pattern of Form C does not change after exposure to DVS experiment at 25° C. and RH up to 95%. In one embodiment, the XRPD pattern of Form C post DVS at 25° C. and RH up to 95% is substantially similar to that set forth in FIG. 22.

In one embodiment, Form C is stable under various storage conditions. In one embodiment, Form C is stable at between approximately 20° C. and approximately 250° C., between approximately 20° C. and approximately 200° C., between approximately 20° C. and approximately 180° C., between approximately 20° C. and approximately 160° C., between approximately 20° C. and approximately 140° C., between approximately 20° C. and approximately 120° C., between approximately 20° C. and approximately 100° C., between approximately 20° C. and approximately 80° C., between approximately 20° C. and approximately 60° C., or between approximately 20° C. and approximately 40° C., for at least one week, two weeks, three weeks, one month, two months, three months, four months, six months, or one year. In one embodiment, Form C is stable at between approximately 60% RH and approximately 98% RH (e.g., 75% RH or 96% RH) for at least one week, two weeks, three weeks, one month, two months, three months, four months, six months, or one year. In one embodiment, Form C is stable under ambient conditions for at least one week, two weeks, three weeks, one month, two months, three months, four months, six months, or one year. In one embodiment, Form C is stable under 20-90° C./60%-98% RH for at least one week, two weeks, three weeks, one month, two months, three months, four months, six months, or one year. In one embodiment, Form C is stable under 25° C./60% RH for at least one week, two weeks, three weeks, four weeks, or eight weeks. In one embodiment, Form C is stable under 40° C./75% RH for at least one week, two weeks, three weeks, four weeks, or eight weeks. In one embodiment, Form C is stable under 55° C./75% RH for at least one week, two weeks, three weeks, four weeks, or eight weeks. In one embodiment, HPLC area percent purity (LCAP) results shows no significant decrease in area percent purity for Form C, in the selected conditions, at the given time points over eight week study, as shown in the table below:

TABLE 6

HPLC results for Form C

| Material | Condition | Area Percent at 248 nm T0 | Area Percent at 248 nm T1 week | Area Percent at 248 nm T2 week | Area Percent at 248 nm T4 week | Area Percent at 248 nm T8 week |
|---|---|---|---|---|---|---|
| Form C | Ambient | 99.8 | 99.8 | 99.8 | 99.8 | 99.9 |
|  | 25° C./60% | 99.8 | 99.9 | 99.9 | 99.8 | 99.9 |
|  | 40° C./75% | 99.8 | 99.8 | 99.8 | 99.9 | 99.9 |
|  | 55° C./75% | 99.8 | 99.9 | 99.8 | 99.8 | 99.9 |

Figure 34:
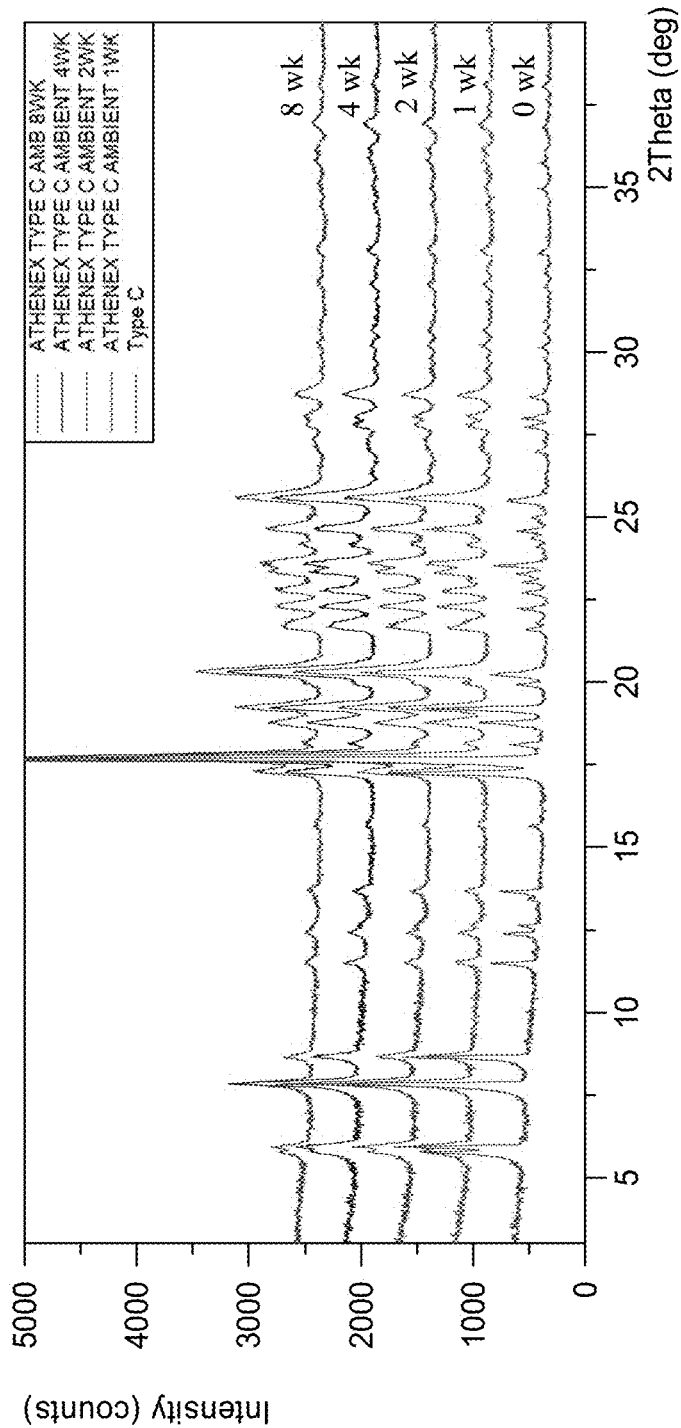
FIG. 34 sets forth an XRPD of Form C in ambient storage condition.
Figure 35:
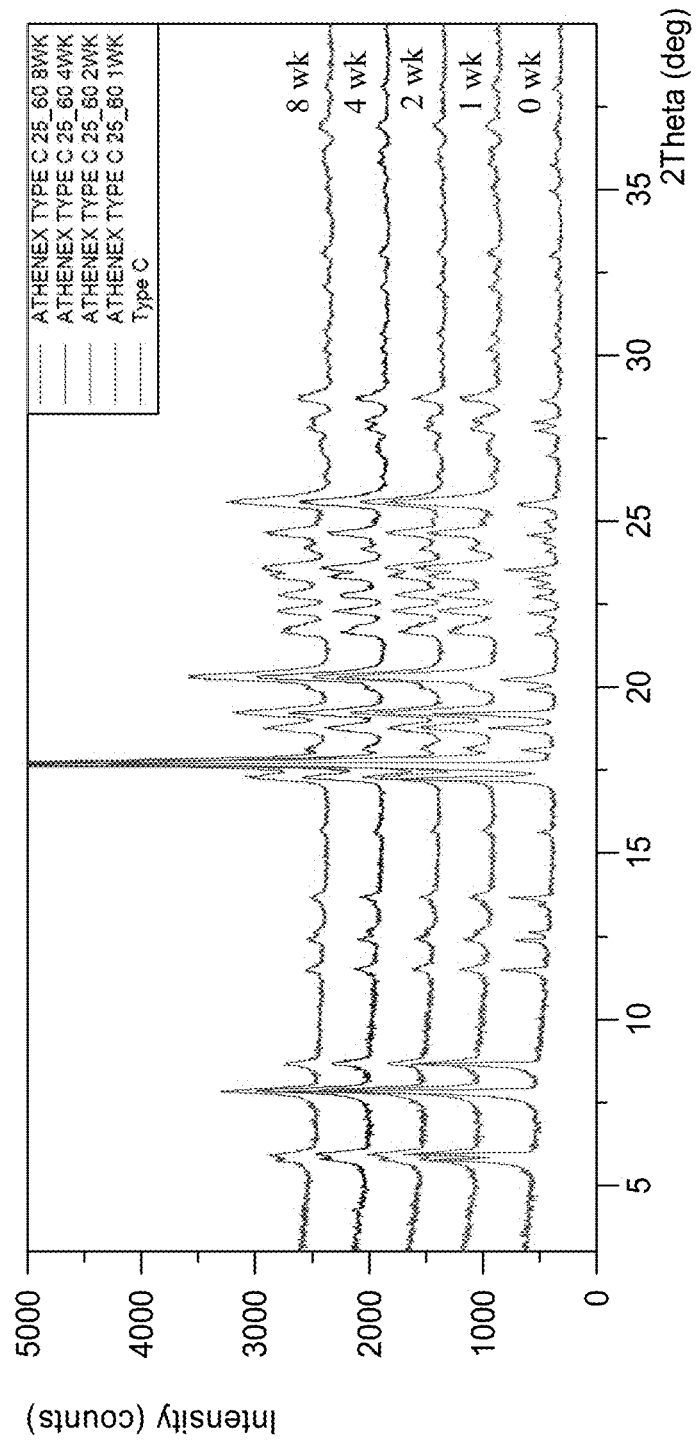
FIG. 35 sets forth an XRPD of Form C in 25° C./60% RH storage condition.
Figure 36:
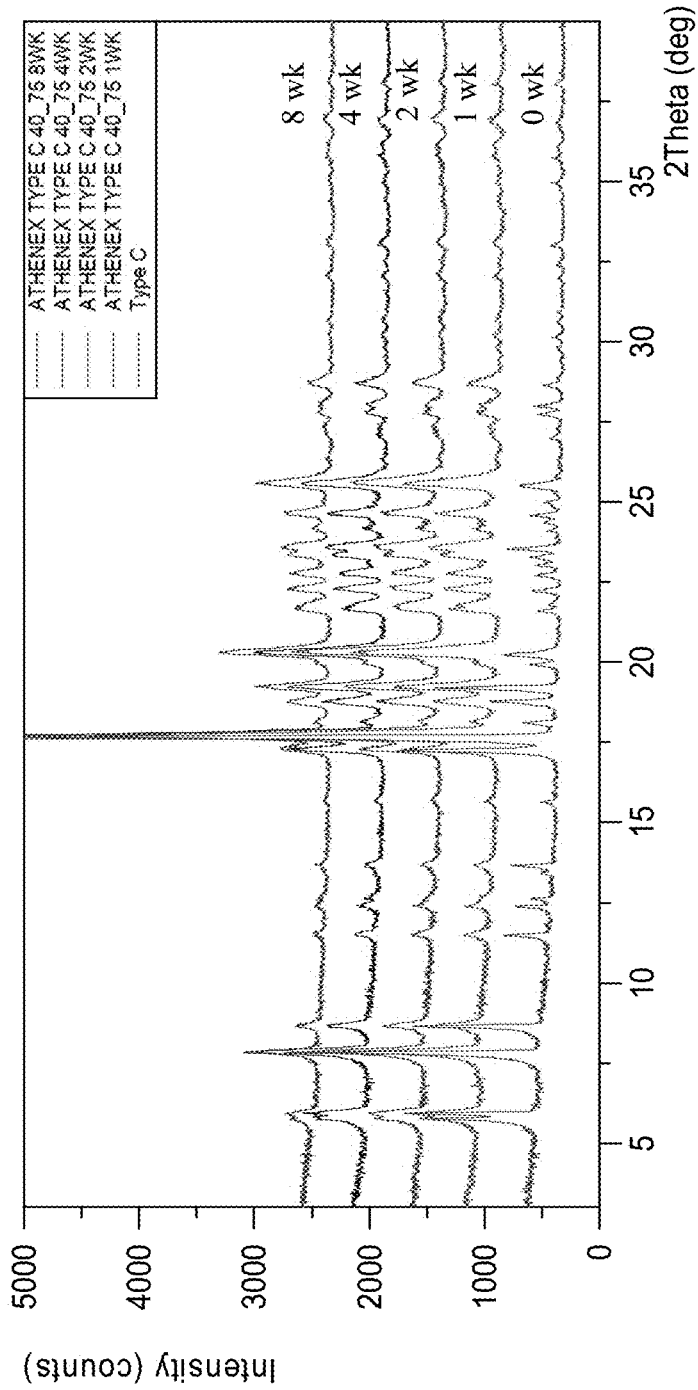
FIG. 36 sets forth an XRPD of Form C in 40° C./75% RH storage condition.
Figure 37:
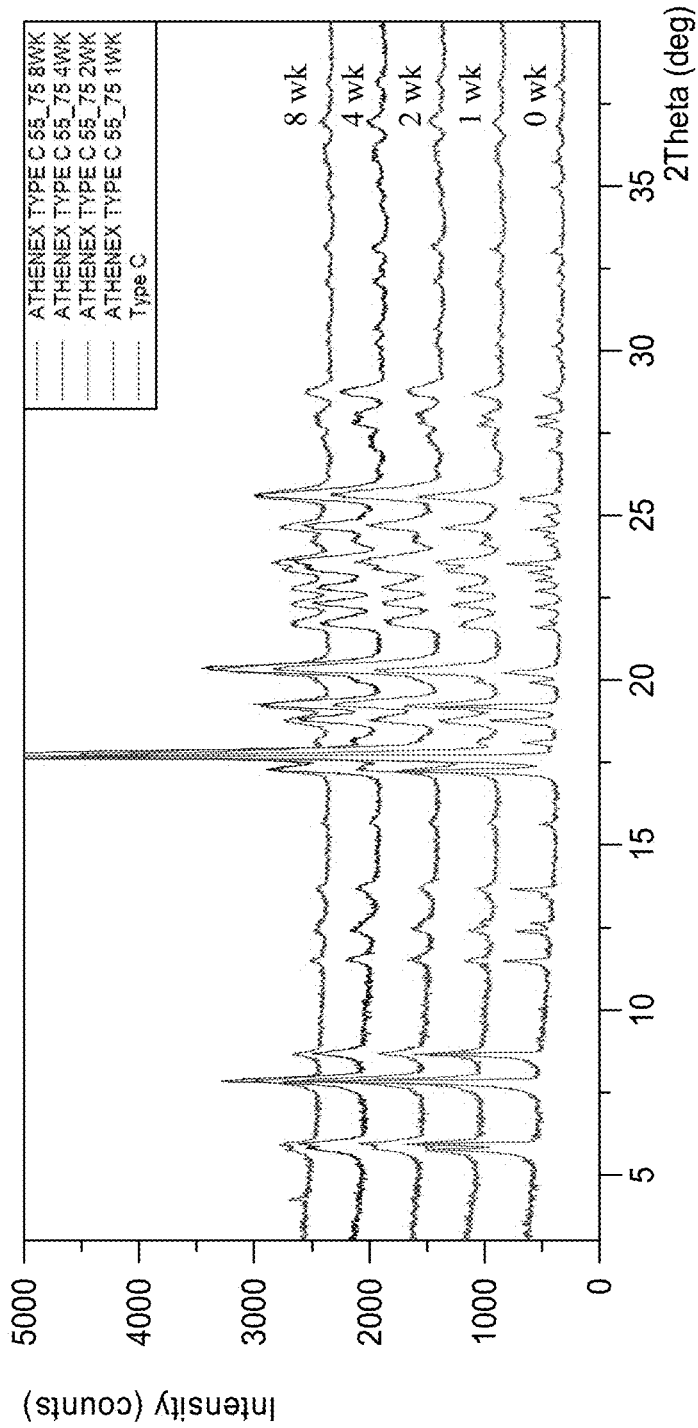
FIG. 37 sets forth an XRPD of Form C in 55° C./75% RH storage condition.

In one embodiment, Form C displays no change in physical form under ambient conditions for at least one week, two weeks, three weeks, four weeks, or eight weeks as set forth in FIG. 34. In one embodiment, Form C displays no change in physical form under 25° C./60% RH for at least one week, two weeks, three weeks, four weeks, or eight weeks as set forth in FIG. 35. In one embodiment, Form C displays no change in physical form under 40° C./75% RH for at least one week, two weeks, three weeks, four weeks, or eight weeks as set forth in FIG. 36. In one embodiment, Form C displays no change in physical form under 55° C./75% RH for at least one week, two weeks, three weeks, four weeks, or eight weeks as set forth in FIG. 37.

In one embodiment, Form C is insoluble in an aqueous solution. In one embodiment, Form C is insoluble in an aqueous solution (e.g., water) at room temperature and when heated to 50° C. (e.g., <1 mg/mL). In one embodiment, Form C is soluble in methanol, ethanol, isopropanol, acetone, MIBK, ethyl acetate, isopropyl acetate, tetrahydrofuran, 2-Me-THF, 1,4-dioxane, acetonitrile, dichloromethane, chloroform, and toluene, and a mixture thereof at room temperature and when heated to 50° C. (e.g., >1 mg/mL). In one embodiment, Form C is insoluble in n-heptane and water at room temperature and when heated to 50° C. (e.g., <1 mg/mL). In one embodiment, Form C is insoluble in MTBE solution at room temperature, but soluble when heated to 50° C.

In one embodiment, Form C is an anhydrate.

In one embodiment, Form C is prepared by slurrying Compound A in a solvent. In one embodiment, Form C is prepared by slurrying Compound A in methanol, ethanol, isopropanol, acetone, MIBK, ethyl acetate, isopropyl acetate, tetrahydrofuran, 2-Me-THF, dioxane, MTBE, acetonitrile, dichloromethane, chloroform, toluene, heptane, water, or a mixture thereof. In one embodiment, Form C is prepared by slurrying Compound A in a mixture of chloroform/MTBE (1:3). In one embodiment, Form C is prepared from slurrying Compound A in a mixture of methanol/water (1:3). In one embodiment, Form C is prepared from slurrying Compound A in a mixture of acetone/heptane (1:3). In one embodiment, Form C is prepared from slurrying Compound A in a mixture of tetrahydrofuran/toluene (1:3). In one embodiment, Form C is prepared from slurrying Compound A in a mixture of dioxane/isopropanol (1:3). In one embodiment, Form C is prepared from slurrying Compound A in a mixture of ethanol/dichloromethane (1:1). In one embodiment, Form C is prepared from slurrying Compound A in a mixture of acetonitrile/ethyl acetate (1:1). In one embodiment, Form C is prepared from slurrying Compound A in a mixture of ethyl acetate/heptane (1:1). In one embodiment, Form C is prepared from slurrying Compound A in a mixture of acetonitrile/water (1:1). In one embodiment, Form C is prepared from slurrying Compound A in a mixture of dichloromethane/MTBE (1:1). In one embodiment, Form C is prepared from slurrying Compound A in a mixture of MIBK/toluene (1:1). In one embodiment, Form C is prepared from slurrying Compound A in a mixture of 2-Me-THF/isopropyl acetate (1:1). In one embodiment, Form C is prepared from slurrying Compound A in a mixture of acetonitrile/isopropanol (1:1). In one embodiment, Form C is prepared from slurrying Compound A in a mixture of ethyl acetate/toluene (1:1). In one embodiment, Form C is prepared from slurrying Compound A in a mixture of methanol/heptane (1:1). In one embodiment, Form C is prepared from slurrying Compound A in a mixture of acetone/water (1:1). In one embodiment, Form C is prepared from slurrying Compound A in a mixture of tetrahydrofuran/MTBE (1:1).

In one embodiment, the slurrying is conducted at room temperature. In one embodiment, the slurrying is conducted with continuous agitation. In one embodiment, slurrying Compound A in chloroform generates a mixture of Form B and Form C. In one embodiment, Form C is slurried in acetonitrile, ethyl acetate, MIBK, dichloromethane, isopropanol, toluene, isopropyl acetate, or heptane at 50° C. In one embodiment, a seed of Form C is added before the slurrying.

In one embodiment, Form C is prepared through solid vapor diffusion. In one embodiment, Form C is prepared by allowing vapor of a solvent to interact with a solid form of Compound A. In one embodiment, Form C is prepared by allowing vapor of a solvent to interact with Compound A for a particular length of time. In one embodiment, Form C is prepared by allowing vapor of a solvent to interact with a solid form of Compound A for 1 day. In one embodiment, Form C is prepared by allowing vapor of a solvent to interact with a solid form of Compound A for 2 days. In one embodiment, Form C is prepared by allowing vapor of a solvent to interact with a solid form of Compound A for 3 days. In one embodiment, Form C is prepared by allowing vapor of a solvent to interact with a solid form of Compound A for 4 days. In one embodiment, Form C is prepared by allowing vapor of a solvent to interact with a solid form of Compound A for 5 days. In one embodiment, Form C is prepared by allowing vapor of a solvent to interact with a solid form of Compound A for 6 days. In one embodiment, Form C is prepared by allowing vapor of a solvent to interact with a solid form of Compound A for 7 days. In one embodiment, Form C is prepared by allowing vapor of a solvent to interact with a solid form of Compound A at room temperature. In one embodiment, Form C is prepared from solid vapor evaporation wherein the solvent is dichloromethane, ethyl acetate, MTBE, acetonitrile, or DMF.

In one embodiment, Form C is prepared through liquid vapor diffusion. In one embodiment, Form C is prepared by allowing vapor of an anti-solvent to diffuse into a concentrated solution of Compound A in a solvent. In one embodiment, the solvent is dichloromethane and the anti-solvent is acetone.

In one embodiment, Form C is prepared through slow cooling of a solution of Compound A.

In one embodiment, Form C is formed by cooling a solution of Compound A in toluene or MIBK. In one embodiment, Form C is formed by slowly cooling a solution of Compound A in a mixture of solvents. In one embodiment, Form C is formed by slowly cooling a solution of Compound A in a mixture of methanol and toluene. In one embodiment, methanol and toluene are mixed at a ratio of about 1:3.

In one embodiment, Form C is prepared from Compound A through polymer-induced crystallization. In one embodiment, Form C is formed by crystallizing a solution of Compound A in a solvent in the presence of a polymer. In one embodiment, Form C is formed by crystallizing a solution of Compound A in a solvent selected from the group consisting of methanol, ethanol, acetone, acetonitrile, chloroform, ethyl acetate, MIBK, isopropanol, and toluene in the presence of a polymer. In one embodiment, Form C is formed by crystallizing a solution of Compound A in the presence of a polymer selected from the group consisting of hypromellose-acetate succinate (HPMC-AS), methylcellulose (MC), polyvinylpyrrolidone/vinyl acetate (PVP-VA), polyvinyl alcohol (PVA), and polyvinylpyrrolidone (PVP). In one embodiment, Form C is formed by crystallizing a solution of Compound A in methanol in the presence of HPMC-AS. In one embodiment, Form C is formed by crystallizing a solution of Compound A in acetonitrile in the presence of HPMC-AS. In one embodiment, Form C is formed by crystallizing a solution of Compound A in ethyl acetate in the presence of PVA. In one embodiment, a mixture of the Form C polymorph and amorphous Compound A is formed by crystallizing a solution of Compound A in ethanol in the presence of MC. In one embodiment, a mixture of the Form C polymorph and amorphous Compound A is formed by crystallizing a solution of a solution of Compound A in acetone in the presence of PVP-VA. In one embodiment, a mixture of the Form C polymorph and amorphous Compound A is formed by crystallizing a solution of Compound A in chloroform in the presence of PVP-VA. In one embodiment, a mixture of the Form C polymorph and amorphous Compound A is formed by crystallizing a solution of Compound A in MIBK in the presence of PVP. In one embodiment, a mixture of the Form C polymorph and amorphous Compound A is formed by crystallizing a solution of Compound A in isopropanol in the presence of HPMC-AS. In one embodiment, a mixture of the Form C polymorph and amorphous Compound A is formed by crystallizing a solution of Compound A in toluene in the presence of MC.

The terms "crystalline polymorphs", "crystal polymorphs", "crystal forms", "polymorphs", or "polymorphic forms" means crystal structures in which a compound (e.g., free base, salts, or solvates thereof) can crystallize in different crystal packing arrangements, all of which have the same elemental composition. Different crystal forms usually have different X-ray diffraction patterns, infrared spectra, melting points, density, crystal shape, optical and electrical properties, stability, and solubility. Crystallization solvent, rate of crystallization, storage temperature, and other factors may cause one crystal form to dominate. Crystal polymorphs of the compounds can be prepared by crystallization under different conditions. In addition, crystal polymorphism may be present but is not limiting, but any crystal form may be a single or a crystal form mixture, or an anhydrous or hydrated crystal form.

The differences in physical properties exhibited by polymorphs are a result of the arrangement or conformation of the molecules in the crystal lattice, and can affect pharmaceutical parameters such as storage stability, compressibility and density (important in formulation and product manufacturing), and dissolution rates (an important factor in bioavailability). Differences in stability can also result from changes in chemical reactivity (e.g., differential oxidation, such that a dosage form discolors more rapidly when comprised of one polymorph than when comprised of another polymorph) or mechanical property (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph may be more likely to form solvates or might be difficult to filter and wash free of impurities (e.g., particle shape and size distribution might be different between polymorphs).

The term "amorphous form" refers to a noncrystalline solid state form of a substance.

Additionally, the compounds of the present application (e.g., free bases and salts, and amorphous forms, crystalline forms, and polymorphs thereof), can exist in either hydrated or unhydrated (the anhydrous) form or as solvates with other solvent molecules or in an unsolvated form. Nonlimiting examples of hydrates include hemihydrates, monohydrates, dihydrates, etc. Nonlimiting examples of solvates include DMSO solvates, DMSO hemisolvates, etc.

All forms of the compounds of the present application are contemplated, either in a mixture or in pure or substantially pure form, including crystalline forms of racemic mixtures and crystalline forms of individual isomers.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing solid forms of a compound, such as polymorphs, include, but are not limited to, differential scanning calorimetry (DSC), X-ray powder diffractometry (XRPD), single crystal X-ray diffractometry, vibrational spectroscopy (e.g., IR and Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. For example, the solvate may be a DMSO solvate, a dichloromethane (DCM) solvate, a methyl ethyl ketone (MEK) solvate, or a tetrahydrofuran (THF) solvate.

As used herein, the terms "unsolvated" or "desolvated" refer to a solid state form (e.g., crystalline forms, amorphous forms, and polymorphs) of a substance which does not contain solvent.

As used herein, the term "pure" means about 90-100%, preferably 95-100%, more preferably 98-100% (wt./wt.), or 99-100% (wt./wt.) pure compound; e.g., less than about 10%, less than about 5%, less than about 2%, or less than about 1% impurity is present. Such impurities include, e.g., degradation products, oxidized products, solvents, and/or other undesirable impurities.

As used herein, a compound is "stable" where significant amount of degradation products are not observed under constant conditions of humidity (e.g., 10%, 20%, 30%, 40%, 50%, 60%, 70%, 75%, 80%, 85%, 90%, and 95% RH), light exposure and temperatures (e.g., higher than 0° C., e.g., 20° C., 25° C., 30° C., 35° C., 40° C., 45° C., 50° C., 55° C., 60° C., 65° C., and 70° C.) over a certain period (e.g., one week, two weeks, three weeks, and four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability. In some embodiments, a compound is less stable if it displays high hygroscopicity (i.e., tendency to absorb water under humid conditions). Accordingly, in some embodiments, the stability of a compound can be measured by assessing its hygroscopicity. A compound is more hygroscopic if it absorbs more water than another compound under the same storage condition (e.g., the same humidity and/or temperature).

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In one embodiment, "approximately" and "about" refer to recited amount, value, or duration±10%, ±8%, ±6%, ±5%, ±4%, ±2%, ±1%, or ±0.5%. In another embodiment, "approximately" and "about" refer to listed amount, value, or duration±10%, ±8%, ±6%, ±5%, ±4%, or ±2%. In yet another embodiment, "approximately" and "about" refer to listed amount, value, or duration±5%. In yet another embodiment, "approximately" and "about" refer to listed amount, value, or duration±2% or ±1%.

When the terms "approximately" and "about" are used when reciting XRPD peaks, these terms refer to the recited X-ray powder diffraction peak±0.3° 2θ, ±0.2 °2θ, or ±0.1 °2θ. In another embodiment, the terms "approximately" and "about" refer to the listed X-ray powder diffraction peak±0.2 °2θ. In another embodiment, the terms "approximately" and "about" refer to the listed X-ray powder diffraction peak±0.1° 2θ.

When the terms "approximately" and "about" are used when reciting temperature or temperature range, these terms refer to the recited temperature or temperature range±5° C., ±2° C., or ±1° C. In another embodiment, the terms "approximately" and "about" refer to the recited temperature or temperature range±2° C.

Methods and Assays

Synthesis of Compound A

Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999.

Methods for preparing the free base of Compound A is described in U.S. Pat. Nos. 7,300,931, 7,851,470, and 7,939,529, the entire contents of each of which are incorporated herein by reference.

X-Ray Powder Diffraction (XRPD)

XRPD analysis is carried out using a diffractometer running in reflection mode. The 2-theta position is calibrated against a standard before running the experiment.

Thermogravimetric/Differential Thermal Analysis (TGA)

Thermogravimetric analysis (TGA) is carried out in an open plate using a thermogravimetric analyzer. The sample is heated from room temperature to 300° C. during which time the change in sample weight is recorded.

Differential Scanning Calorimetry (DSC)

Differential Scanning calorimetry (DSC) is carried out in a sealed plate using a differential scanning calorimeter. The sample and reference are heated from room temperature to 300° C. and the resulting heat flow response is monitored.

Dynamic Vapor Sorption (DVS)

Dynamic Vapor Sorption (DVS) was measured using a SMS (Surface Measurement Systems) DVS Intrinsic. The test was performed at 25° C. while the RH was varied from 0% to 95% at 10% increments in the range of 0% RH-90% RH and at 5% increment up to 95% RH. The change in mass after each increase or decrease in the RH was recorded as a percentage of the original mass of the starting material.

High-Performance Liquid Chromatography (HPLC) Analysis

High-performance Liquid Chromatography (HPLC) analysis was performed to determine the chemical stability of Forms A, B, and C of Compound A after storage at various conditions, using an Agilent 1100 system with DAD. Chemical stability was estimated by measuring and comparing the area percent of the material peak at various time points.

Solubility Estimation

Solubility of the solid forms of the present application in a variety of solvents is measured. Solvent is added to a sample until the total volume reaches 100 µL, followed by 100 µL per step until the sample is dissolved or the concentration is less than <1.0 mg/mL. The approximate solubility is then calculated.

Polymorph Screening Methods

Slurry

Compound A is suspended in solvent and stirred. Solids prepared by slurry are then isolated and analyzed by various methods for the characterization of the solids, such as XRPD.

Anti-Solvent Addition

A concentrated stock of Compound A in various solvents is prepared. The solution is stirred, and anti-solvent is quickly added to induce precipitation. Solids are then isolated and analyzed by various methods for the characterization of the solids, such as XRPD.

Slow Cooling

A concentrated stock of Compound A in various solvents is prepared, heated, and slowly cooled to induce precipitation. Solids are then isolated and analyzed by various methods for the characterization of the solids, such as XRPD.

Liquid Vapor Diffusion

A concentrated stock of Compound A in various solvents is prepared in an inner vial, which is placed inside a sealed larger vial containing anti-solvent. Solids are then isolated and analyzed by various methods for the characterization of the solids, such as XRPD.

Solid Vapor Diffusion

A sample of Compound A is prepared in an inner vial, which is placed inside a larger vial containing a volatile solvent and sealed. The system is maintained at room temperature, allowing the solvent vapor to interact with the solid. Solids are then isolated and analyzed by various methods for the characterization of the solids, such as XRPD.

Polymer Induced Crystallization

A sample of Compound A is prepared in a glass vial. A pre-determined amount of a selected solvent is then added to dissolve the sample, followed by addition of a polymer. Solids are then isolated and analyzed by various methods for the characterization of the solids, such as XRPD.

Pharmaceutical Compositions

The present application also provides pharmaceutical compositions comprising one or more compounds of the present application (e.g., solid forms, amorphous forms, crystalline forms, and polymorphs of Compound A) in combination with at least one pharmaceutically acceptable excipient or carrier. In one embodiment, the pharmaceutical composition comprises a solid form of Compound A of the present application and a pharmaceutically acceptable excipient, wherein the pharmaceutical composition is formulated for topical administration.

A "pharmaceutical composition" is a formulation containing the compounds of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the one or more of the disclosed compounds) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches, and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the present application is formulated to be compatible with its intended route of administration. Examples of routes of administration include parenteral (e.g., intravenous), intradermal, subcutaneous, oral (e.g., inhalation), transdermal, topical, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the present application can be administered to a subject in many of the well-known methods currently used for treatment. For example, for treatment of cancers, a compound of the present application may be injected directly into tumors, injected into the blood stream or body cavities, taken orally, or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

A pharmaceutical composition of the present application may also be formulated for topical administration. The topical compositions may be administered to an affected area of the subject, such as skin. The affected area of the skin may be located at one or more locations independently selected from the scalp, forehead, forearm, face, nose, ears, eye lids, lips, neck, arms, hands, trunk, legs, and feet. In one embodiment, there may be more than one affected area. In one embodiment, there may be more than one affected area located at one or more locations independently selected from the scalp, forehead, forearm, face, nose, ears, eye lids, lips, neck, arms, hands, trunk, legs, and feet.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5,000 mg/kg per day. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present application are administered topically, orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the present application. Based on the present application the skilled artisan can identify and employ other components and methodology useful for practicing the present application.

Methods of Treatment

The present application provides methods for the treatment of a cell proliferative disorder in a subject in need thereof by administering to the subject a therapeutically effective amount of one or more compounds of the present application (e.g., solid forms, amorphous forms, crystalline forms, or polymorphs). The present application also provides methods of protecting against a cell proliferative disorder in a subject in need thereof by administering to the subject a therapeutically effective amount of one or more compounds of the present application (e.g., solid forms, amorphous forms, crystalline forms, or polymorphs). The cell proliferative disorder can be cancer or a precancerous condition. The present application further provides the use of one or more compounds of the present application for the preparation of a medicament useful for the treatment or prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. A "subject" includes a mammal. The mammal can be any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration. A cell proliferative disorder includes a precancer or a precancerous condition. A cell proliferative disorder includes cancer.

Exemplary cell proliferative disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; actinic keratosis; actinic keratosis (solar keratosis); ichthyosis; atopic dermatitis; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, hairy cell leukemia, lip and oral cavity cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine corpus cancer, vaginal cancer, vulvar cancer, and Wilm's Tumor.

Actinic keratosis, i.e., "AK," is a common precancerous skin condition caused by excessive exposure to ultraviolet light. AKs are rough, dry, tan-, pink-, or red-colored blemishes (lesions) that often appear on the parts of the head, including the face, throat, neck, nose, forehead, ears, or lips. AKs may also appear or other body parts that receive prolonged, intense sunlight, e.g., the hands, the back, and other areas on the trunk and legs. AKs are most common in fair-skinned, middle-aged or elderly individuals. A subject suffering from AKs may have a single lesion or multiple lesions. AK can lead to squamous cell carcinoma.

As used herein, the term "trunk" refers to the portion of a subject that is not an arm, a leg, or the head.

Clinical variants of AK include: classic (or common), hypertrophic (or hyperkeratotic), atrophic, AK with cutaneous horn, pigmented AK, actinic cheilitis, and Bowenoid AK. Unless explicitly indicated otherwise, the methods described herein are applicable to all clinical variants, including those listed herein.

Treatments for AK include cryosurgery, surgical excision and/or scraping of the affected areas, photodynamic therapy, and topical formulations (e.g., creams, gels, patches, etc.) comprising a steroid, fluorouracil, diclofenac, imiquimod, 5-aminolaevulinic acid (Ameluz®). The approved treatment for AK is Picato (Ingenol Mebutate)®, a gel containing ingenol mebutate (0.015% or 0.05%). The gel is applied to the affected areas on the face or scalp once daily for three consecutive days (0.015%), or on the trunk or extremities once daily for two consecutive days (0.05%).

The skin toxicity associated with the use of other AK treatments, such as with Picato (Ingenol Mebutate)®, is known to produce unwanted side effect or adverse reactions, i.e., local skin reactions (LSRs), which include vesiculation, postulation, erosion, ulceration, redness, swelling, flaking, scaling, hard lumps, dryness, pus, and blistering. Other side effects include application site pain, application site pruritus, application site irritation, application site swelling, application site burning sensation, application site infection, periorbital edema, nasopharyngitis, chills, sore throat, drooping eyes, puffy eyes, hypopigmentation, hyperpigmentation, and headache.

The present application provides a method of treating or preventing a disease or condition (e.g., a cell proliferative disorder) in which a tyrosine kinase (e.g., an Src tyrosine kinase) plays a role, comprising administering, to a subject in need thereof, a therapeutically effective amount of a composition comprising any one of the solid forms of Compound A as described herein.

The present application also provides a solid form of Compound A as described herein in treating or preventing a disease or condition (e.g., a cell proliferative disorder) in which a tyrosine kinase (e.g., an Src tyrosine kinase) plays a role in a subject in need thereof.

The present application also provides a solid form of Compound A as described herein for use in the manufacture of a medicament for the treatment or prevention of a disease or condition (e.g., a cell proliferative disorder) in which a tyrosine kinase (e.g., an Src tyrosine kinase) plays a role in a subject in need thereof.

The present application also provides use of a solid form of Compound A as described herein in the manufacture of a medicament for the treatment or prevention of a disease or condition (e.g., a cell proliferative disorder) in which a tyrosine kinase (e.g., an Src tyrosine kinase) plays a role in a subject in need thereof.

In one embodiment, the disease or condition is a precancer (e.g., a precancerous condition as described herein). In one embodiment, the disease or condition is cancer (e.g., a cancerous condition as described herein). In one embodiment, the disease or condition is AK.

In one embodiment, the solid forms of the present application is administered, or for administration, or for manufacture of a medicament for administration to a subject in need thereof topically.

In one embodiment, the present application provides a method of treating or preventing actinic keratosis or psoriasis, comprising administering to a subject in need thereof a therapeutically effective amount of the solid forms of the present application.

In one embodiment, for any of the methods disclosed in this application, the solid forms of Compound A are administered to an affected area of the subject, wherein the affected area is the skin.

In one embodiment, for any of the methods disclosed in this application, the administration of the solid forms of Compound A reduces the number and/or severity of local skin reactions or other adverse side effects in the subject compared to other treatments of actinic keratosis or psoriasis. In one embodiment, the other treatment of actinic keratosis or psoriasis comprises the topical administration of ingenol mebutate.

In one embodiment, for any of the methods disclosed in this application, the administration of the solid forms of Compound A reduces the number of the subjects that have local skin reactions or other adverse side effects compared to other treatments of actinic keratosis or psoriasis.

In one embodiment, for any of the methods disclosed in this application, the local skin reaction is selected from the group selected from vesiculation, postulation, erosion, ulceration, redness, swelling, flaking, scaling, hard lumps, dryness, pus, and blistering.

In one embodiment, for any of the methods disclosed in this application, the other side effect is selected from the group consisting of application site pain, application site pruritus, application site irritation, application site swelling, application site burning sensation, application site infection, periorbital edema, nasopharyngitis, chills, sore throat, drooping eyes, puffy eyes, hypopigmentation, hyperpigmentation, and headache.

In one embodiment, the present application relates to treating or treatment of a disease or condition as described herein (e.g., AK). In one embodiment, the present application relates to preventing or prevention of a disease or condition as described herein (e.g., AK).

Definitions

As used herein, "treating" or "treat" describes the management and care of a patient for the purpose of combating a disease, condition, or disorder, and includes the administration of a compound of the present application to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of a compound of the present application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "symptom" is defined as an indication of disease, illness, injury, or that something is not right in the body. Symptoms are felt or noticed by the individual experiencing the symptom, but may not easily be noticed by others.

As used herein, the term "sign" is also defined as an indication that something is not right in the body. However, signs are defined as things that can be seen by a doctor, nurse, or other health care professional.

EXAMPLES

Example 1: X-Ray Powder Diffraction (XRPD)

XRPD analysis was carried out on a Panalytical X'Pert[3] Powder XRPD on a Si zero-background holder, scanning the samples between 3 and 40° 2-theta. The 2-theta position was calibrated against Panalytical 640 Si powder standard. The test material was gently compressed on a glass disc inserted into a sample holder. The sample was then loaded into a Panalytical X'Pert[3] Powder XRPD diffractometer running in reflection mode and analyzed, using the following experimental conditions.

| | |
|---|---|
| Start Position [°2Th.] | 3.0000 |
| End Position [°2Th.] | 40.0000 |
| Step Size [°2Th.] | 0.0131 |
| Scan Speed [°/s] | 0.16 |
| Scan Mode | Continuous |
| Divergence Slit | Automatic |
| Anode Material | Cu |
| K-Alpha1 [Å] | 1.540598 |
| K-Alpha2 [Å] | 1.544426 |
| K-A2/K-A1 Intensity Ratio | 0.50000 |
| X-Ray Tube Settings | 40 mA, 45 kV |
| Method Duration [min] | 4 |

Example 2: Thermogravimetric/Differential Thermal Analysis (TGA)

The test material was weighed into an open platinum plate and loaded into a TA Instruments TA Q500 thermogravimetric/analyzer (TGA). The sample was then heated at a rate of 10° C./min from room temperature to 300° C. during which time the change in sample weight was recorded. Nitrogen was used as the purge gas, at a sample purge flow rate of 15 $cm^3$/min and a balance purge flow rate of 25 $cm^3$/min.

Example 3: Differential Scanning Calorimetry (DSC)

The test material was weighed into an aluminum DSC pan and sealed by crimping. The sample pan was then loaded into a TA Instruments TA Q2000 DSC. Once a stable heat-flow response was obtained, the sample and reference were heated from room temperature to 300° C. at scan rate of 10° C./min and the resulting heat flow response was monitored. Nitrogen was used as the purge gas.

Example 4: Dynamic Vapor Sorption (DVS)

Dynamic Vapor Sorption (DVS) was measured using a SMS (Surface Measurement Systems) DVS Intrinsic, using the following parameters:

| | |
|---|---|
| Temperature | 25° C. |
| Sample Size | 10-20 mg |
| Gas and flow rate | $N_2$, 200 mL/min |
| dm/dt | 0.002%/min |
| Min. dm/dt stability duration | 10 min |
| Max equilibrium time | 180 min |
| RH range | 0% RH-95% RH-0% RH |
| RH step size | 10% (0% RH-90% RH) then 5% (90% RH-95% RH) |

Example 5: High-Performance Liquid Chromatography (HPLC) Analysis

For High-performance Liquid Chromatography (HPLC) analysis, an Agilent 1100 system with DAD was used. The method parameters used are listed in the table below:

TABLE 7

HPLC method parameters

| HPLC Method | Parameters | | |
|---|---|---|---|
| Instrument | Agilent 1100 with DAD detector | | |
| Column | Thermo Hypersil Gold, 150 × 4.6 mm, 3 μm | | |
| Mobile phase | A: 0.05% TFA in Water | | |
| | B: 0.05% TFA in ACN | | |
| Gradient | Time (min) | A % | B % |
| | 0.0 | 95 | 5 |
| | 20.0 | 30 | 70 |
| | 21.0 | 0 | 100 |
| | 22.0 | 0 | 100 |
| | 22.5 | 95 | 5 |
| | 30 | 95 | 5 |
| Run time | 30 min | | |
| Flow rate | 1.0 mL/min | | |
| Wave length | 248 nm | | |
| Injection volume | 10 μL | | |
| Column temperature | 30° C. | | |
| Diluent | Acetonitrile/Water (1:1) | | |

Example 6: Solubility Estimation

Solubility of the solid forms of the present application in a variety of solvents was measured according to the following procedures. A sample (~2 mg) was weighed into a 4-mL glass vial. Solvent was added into the vial stepwise at 50 μL per step until the total volume was 100 μL, followed by 100 μL per step until concentration was less than 1.0 mg/mL. The solutions were mixed thoroughly after each addition by sonication for 2 minutes and vortexing for 1 minute. The addition of solvent was complete if the sample was dissolved or the concentration was <1.0 mg/mL. The volumes of solvent (V1 and V2) were recorded, and approximate solubility was calculated.

Example 7: Polymorph Screening Methods

Slurry

Approximately 5 to 20 mg of Compound A was suspended in 0.1-0.5 mL solvent in a 1.5 or 3.0-mL glass vial. The suspension was stirred at target temperature (room temperature or 50° C.) at 200 rpm. Solids for XRPD analysis were isolated via centrifugation at 14,000 rpm for 5 minutes at room temperature. If no solid or gel was obtained, the slurry was transferred to a fume hood for evaporation.

Anti-Solvent Addition

A concentrated stock of Compound A in solvent was prepared. The solution was stirred, and anti-solvent was quickly added to induce precipitation. Solids for XRPD analysis were isolated by filtration or centrifugation. If no solid was obtained, the solution was transferred to a fume hood for evaporation.

Slow Cooling

A concentrated stock of Compound A in solvent was prepared. The suspension was heated to 50° C. and held at 50° C. for at least 30 minutes. The solution or suspension was then filtered at 50° C. using a 0.45 micron PTFE filter, and the filtrates were collected in clean vials. The solutions were cooled to 5° C. to induce precipitation. Solids for XRPD analysis were isolated by filtration or centrifugation. Samples which did not precipitate were cooled to −20° C. to induce precipitation.

Liquid Vapor Diffusion

A concentrated stock of Compound A in solvent was prepared in a vial. This inner vial was placed inside a sealed larger vial containing anti-solvent. Solids for XRPD analysis were isolated by filtration or centrifugation.

Solid Vapor Diffusion

A 5-15 mg sample of Compound A was weighed in a small vial (e.g., 3-mL). This inner vial was placed inside a larger vial (e.g., 20-mL) containing 3-4 mL of a volatile solvent. The outer vial was then sealed. The system was maintained at room temperature for 7 days, allowing the solvent vapor to interact with the solid. The resulting solids were isolated and analyzed by XRPD.

Polymer Induced Crystallization

A 5-15 mg sample of Compound A was weighed in a glass vial. A pre-determined amount of a selected solvent was then added to dissolve the sample. The corresponding polymer was then added to the vial, and the samples were stirred at room temperature for 7 days. The resulting solids were isolated and analyzed by XRPD.

Example 8: Characterization of Form C

Figure 1:
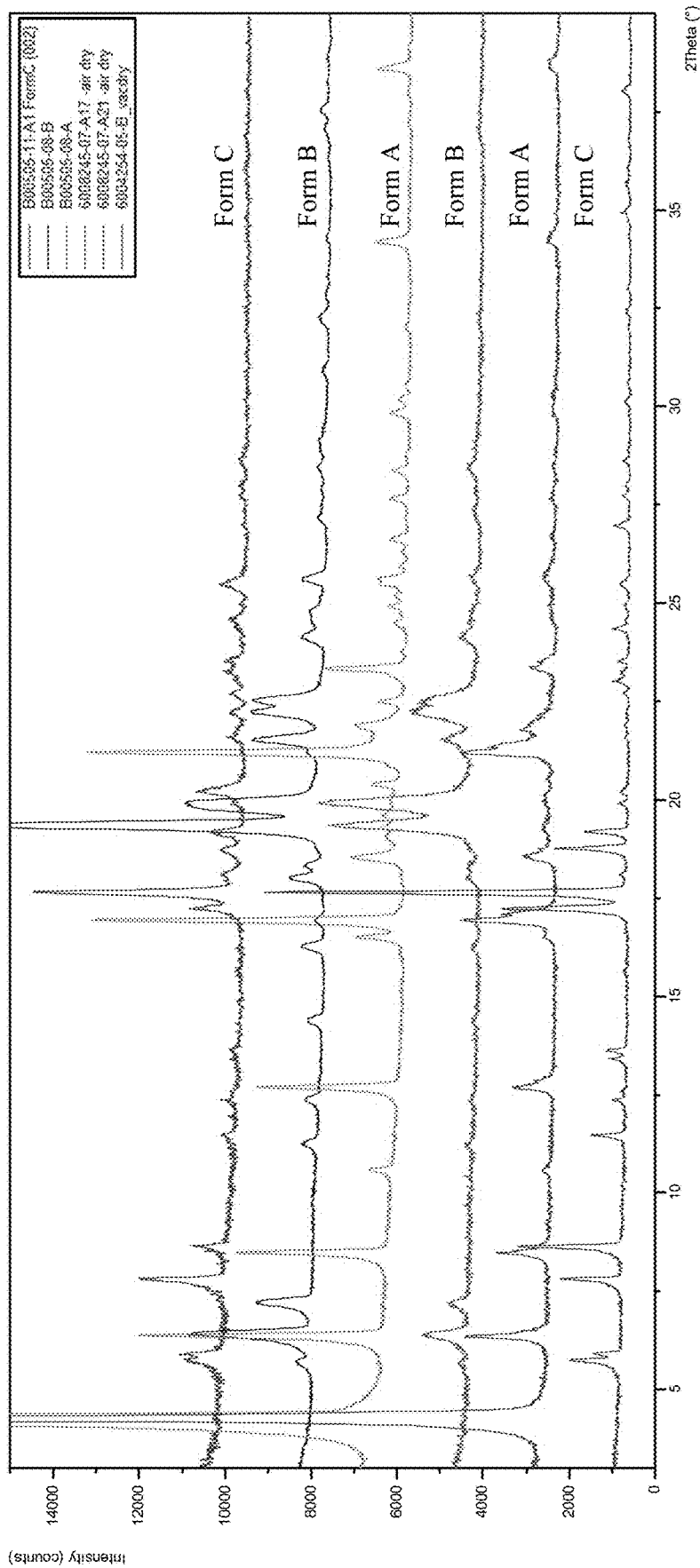
FIG. 1 sets forth an XRPD overlay of Forms A, B, and C as previously identified and as generated from screening.
Figure 2:
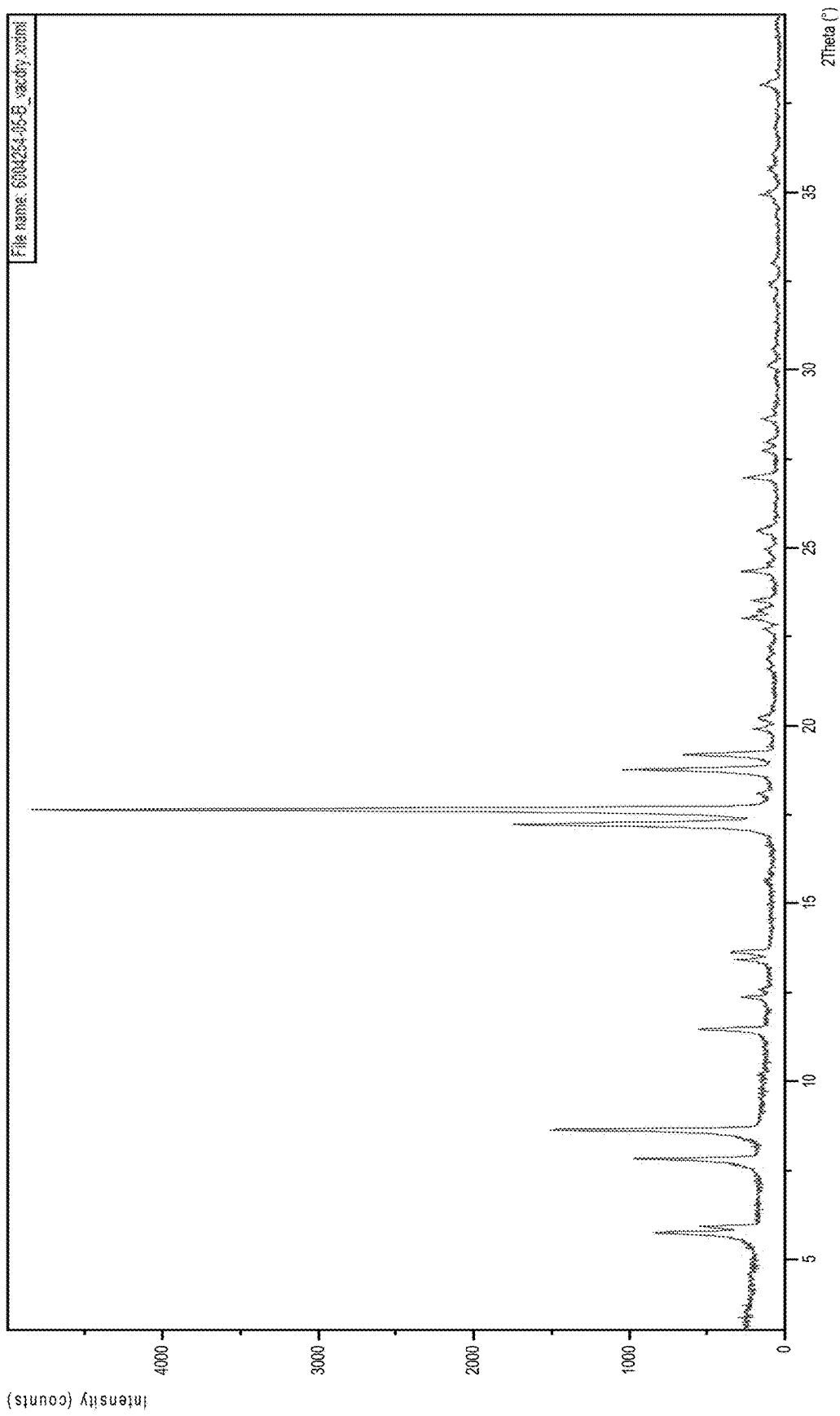
FIG. 2 sets forth an XRPD of Form C.

Form C was characterized by XRPD, TGA, and DSC (as described above). The XRPD analysis of Form C is shown in FIG. 2.

Figure 3:
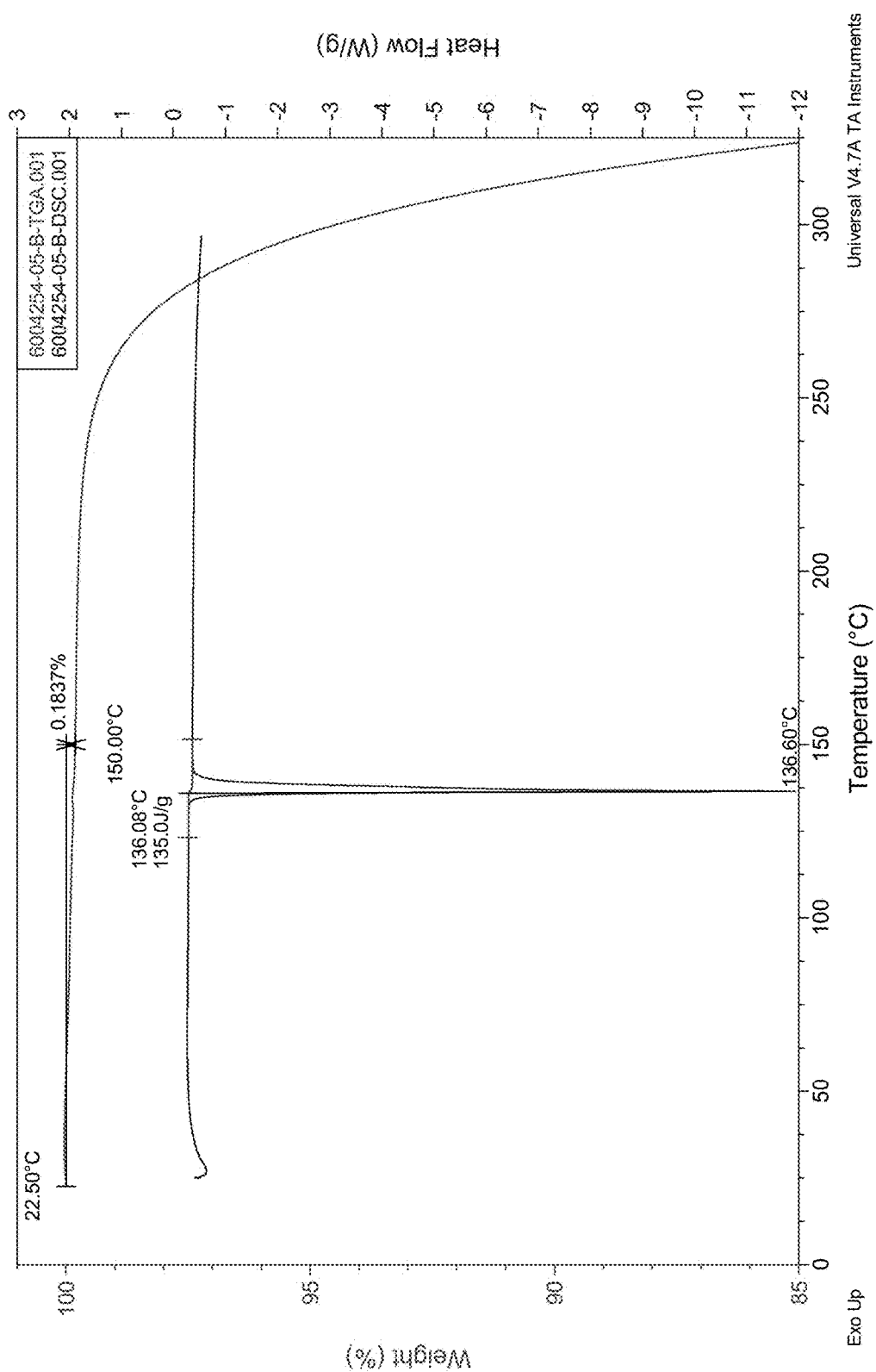
FIG. 3 sets forth a DSC/TGA overlay of Form C.

Form C displayed an endotherm at 136° C. (FIG. 3) as measured by DSC. Form C showed 0.18% weight loss before 150° C. as measured by TGA, matching with the state of an anhydrate (FIG. 3).

Example 9: Solubility of Form C

Solubility of Form C was estimated in solvents according to the methods described above, and the results are listed in Table 8.

TABLE 8

Solubility of Form C in selected solvents

| Solvent | Solubility (mg/mL) |
|---|---|
| MeOH | 9.58-19.15 |
| EtOH | 5.14-6.42 |
| IPA | 1.30-1.39 |
| Acetone | 5.69-8.59 |
| MIBK | 1.61-1.76 |
| EtOAc | 2.37-2.63 |
| IPAc | 1.08-1.15 |
| THF | 11.0-22.0 |
| 2-MeTHF | 5.10-6.38 |
| 1,4-Dioxane | 12.6-25.1 |
| MTBE | <1.00* |
| ACN | 4.43-5.54 |
| DCM | 1.33-1.44 |
| CHCl$_3$ | 25.9-51.8 |
| toluene | 1.51-1.61 |
| n-Heptane | <1.00 |
| H2O | <1.00 |

*Dissolved after heating to 50° C. for 2 hours.

Example 10: Slurry-Based Polymorph Screening

Compound A was slurried according to the methods described above. The resulting solids were analyzed by XRPD and identified for physical state. The results are listed in Table 9.

Figure 4:
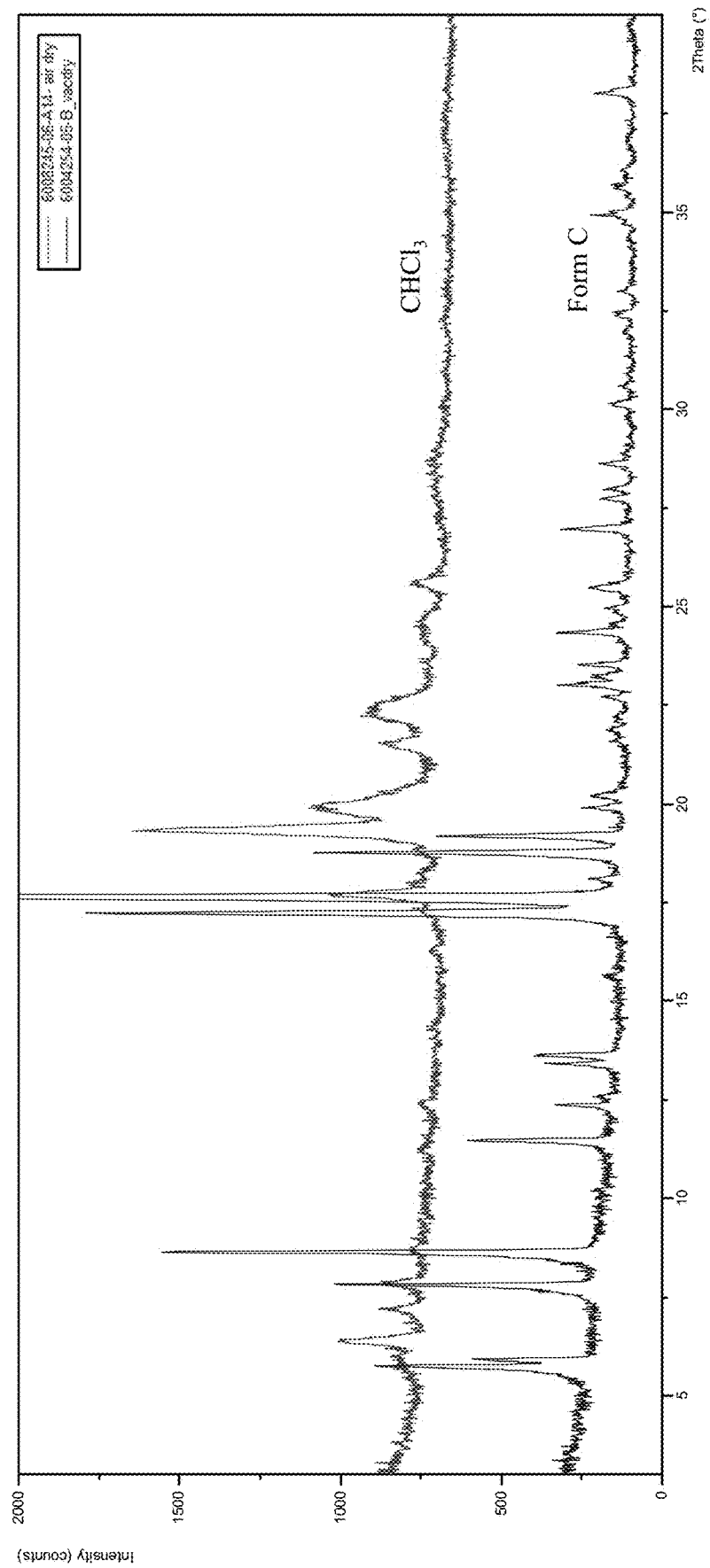
FIG. 4 sets forth an XRPD overlay of a mixture of Forms C and B from solvent slurry experiments.
Figure 5:
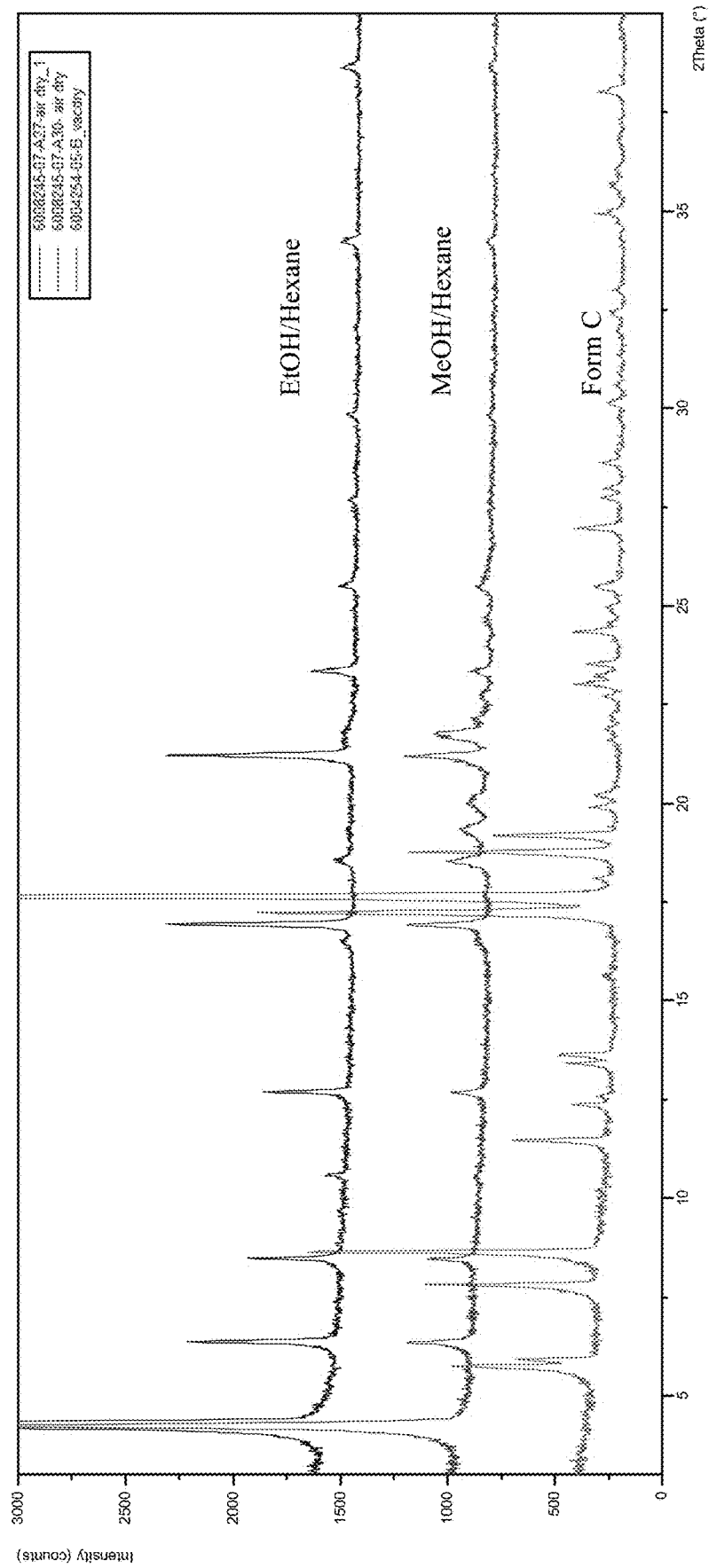
FIG. 5 sets forth an XRPD overlay of Form A from liquid vapor diffusion experiments.

The slurries were screened at room temperature and 50° C., and exhibited similar XRPD patterns corresponding to Form C. The slurry in chloroform at room temperature yielded Form C+B (FIG. 4).

TABLE 9

Summary of slurry based polymorph screening experiments

| Temp. | Solvent | Cmpd A (mg) | Solvent (mL) | Polymorph Form |
|---|---|---|---|---|
| RT | MeOH | 15.9 | 0.1 | C |
| RT | EtOH | 14.5 | 0.1 | C |
| RT | IPA | 15.4 | 0.1 | C |
| RT | Acetone | 16.5 | 0.1 | C |
| RT | MIBK | 15.7 | 0.1 | C |
| RT | EtOAc | 14.5 | 0.1 | C |
| RT | IPAc | 18.7 | 0.1 | C |
| RT | THF | 15.3 | 0.1 | C |
| RT | 2-Me-THF | 17.9 | 0.1 | C |
| RT | Dioxane | 16.7 | 0.1 | C |
| RT | MTBE | 15.7 | 0.1 | C |
| RT | ACN | 18.6 | 0.1 | C |
| RT | DCM* | 14.7 | 0.1 | C |
| RT | CHCl$_3$* | 18.1 | 0.1 | C + B |
| RT | Toluene | 16.3 | 0.1 | C |
| RT | Heptane | 17.3 | 0.2 | C |
| RT | Water | 14.6 | 0.2 | C |
| RT | CHCl$_3$/MTBE (1:3) | 14.0 | 0.2 | C |
| RT | MeOH/Water (1:3) | 16.2 | 0.2 | C |
| RT | Acetone/Heptane (1:3) | 18.9 | 0.2 | C |
| RT | THF/Toluene (1:3) | 17.2 | 0.2 | C |
| RT | Dioxane/IPA (1:3) | 14.8 | 0.2 | C |
| RT | EtOH/DCM (1:1)* | 15.7 | 0.1 | C |
| RT | 2-Me-THF/MIBK (1:1) | 15.6 | 0.2 | C |
| RT | ACN/EtOAc (1:1) | 14.7 | 0.2 | C |
| RT | EtOAc/Heptane (1:1) | 16.9 | 0.2 | C |
| RT | ACN/Water (1:1) | 17.4 | 0.2 | C |
| RT | DCM/MTBE (1:1) | 14.2 | 0.2 | C |
| RT | MIBK/Toluene (1:1) | 15.5 | 0.2 | C |
| RT | 2-Me-THF/IPAc (1:1) | 16.3 | 0.2 | C |
| RT | ACN/IPA (1:1) | 15.8 | 0.2 | C |
| RT | EtOAc/Toluene (1:1) | 16.0 | 0.2 | C |
| RT | MeOH/Heptane (1:1) | 15.1 | 0.2 | C |
| RT | Acetone/Water (1:1) | 14.7 | 0.2 | C |
| RT | THF/MTBE (1:1) | 18.2 | 0.2 | C |
| 50° C. | ACN | 14.4 | 0.1 | C |
| 50° C. | EtOAc | 16.2 | 0.1 | C |
| 50° C. | MIBK | 16.8 | 0.1 | C |
| 50° C. | DCM* | 17.4 | 0.1 | C |
| 50° C. | IPA | 16.9 | 0.1 | C |
| 50° C. | Toluene | 17.0 | 0.1 | C |
| 50° C. | IPAc | 16.8 | 0.1 | C |
| 50° C. | Heptane | 17.1 | 0.2 | C |
| 50° C. | Water | 16.3 | 0.2 | C |
| 50° C. | MTBE | 16.8 | 0.1 | C |

*solution observed for 7 days before evaporation

Example 11: Vapor Diffusion

Compound A was prepared for liquid and solid vapor diffusion experiments according to the methods described above. The resulting solids were analyzed by XRPD and identified for physical state (Tables 10 and 11).

Figure 6:
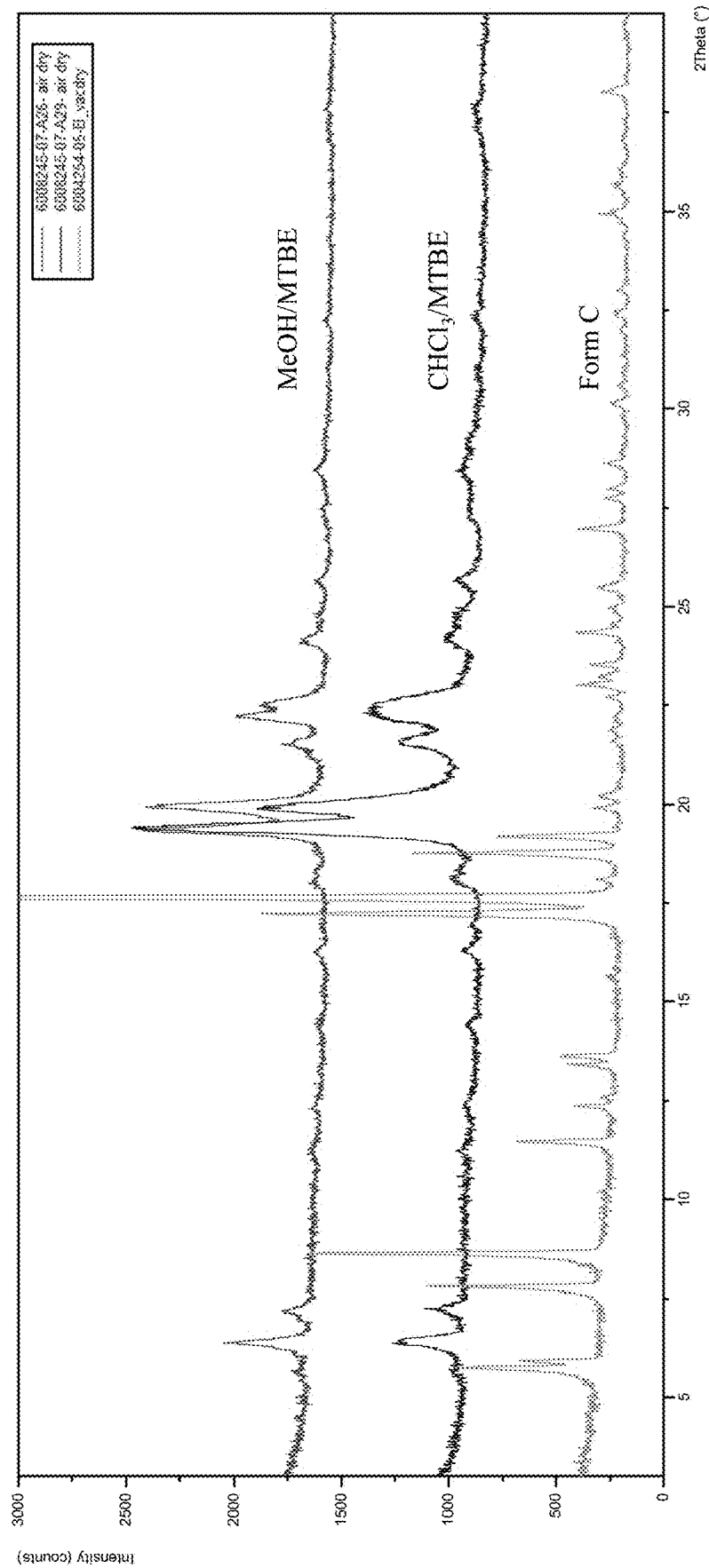
FIG. 6 sets forth an XRPD overlay of Form B from liquid vapor diffusion experiments.
Figure 7:
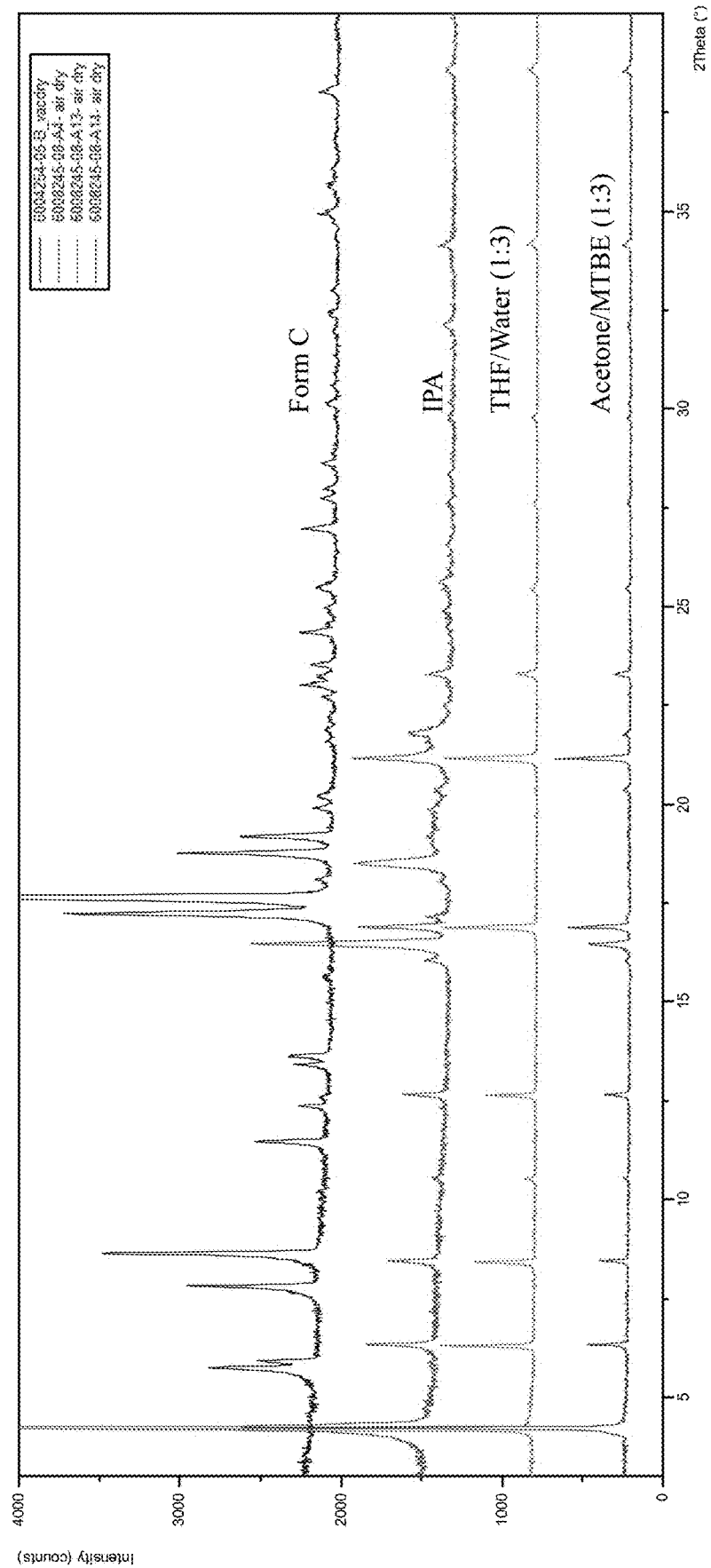
FIG. 7 sets forth an XRPD overlay of Form A from slow cooling experiments.

Solid vapor diffusion experiments yielded Form C. Liquid vapor diffusion methods yielded Form A with EtOH/Hexane and MeOH/Hexane (FIG. 5), and Form B with MeOH/MTBE and CHCl$_3$/MTBE (FIG. 6).

TABLE 10

Summary of solid vapor diffusion experiments

| Temperature | Cmpd A (mg) | Anti-Solvent | Anti-Solvent (mL) | Polymorph Form |
|---|---|---|---|---|
| RT | 15.2 | DCM | 3 | C |
| RT | 14.6 | EtOAc | 3 | C |
| RT | 17.4 | MTBE | 3 | C |
| RT | 15.5 | ACN | 3 | C |
| RT | 16.2 | DMF | 3 | C |

TABLE 11

Summary of liquid vapor diffusion experiments

| Temperature | Cmpd A (mg) | Solvent | Solvent (mL) | Anti-Solvent | Anti-Solvent (mL) | Crystal Type |
|---|---|---|---|---|---|---|
| RT | 15.7 | MeOH | 1.1 | MTBE | 3 | B |
| RT | 16.4 | EtOH | 2.0 | Hexane | 3 | A |
| RT | 18.1 | DCM | 0.3 | Acetone | 3 | C |
| RT | 15.6 | CHCl3 | 0.3 | MTBE | 3 | B |
| RT | 16.8 | MeOH | 1.2 | Hexane | 3 | A |

Example 12: Slow Cooling

Figure 8:
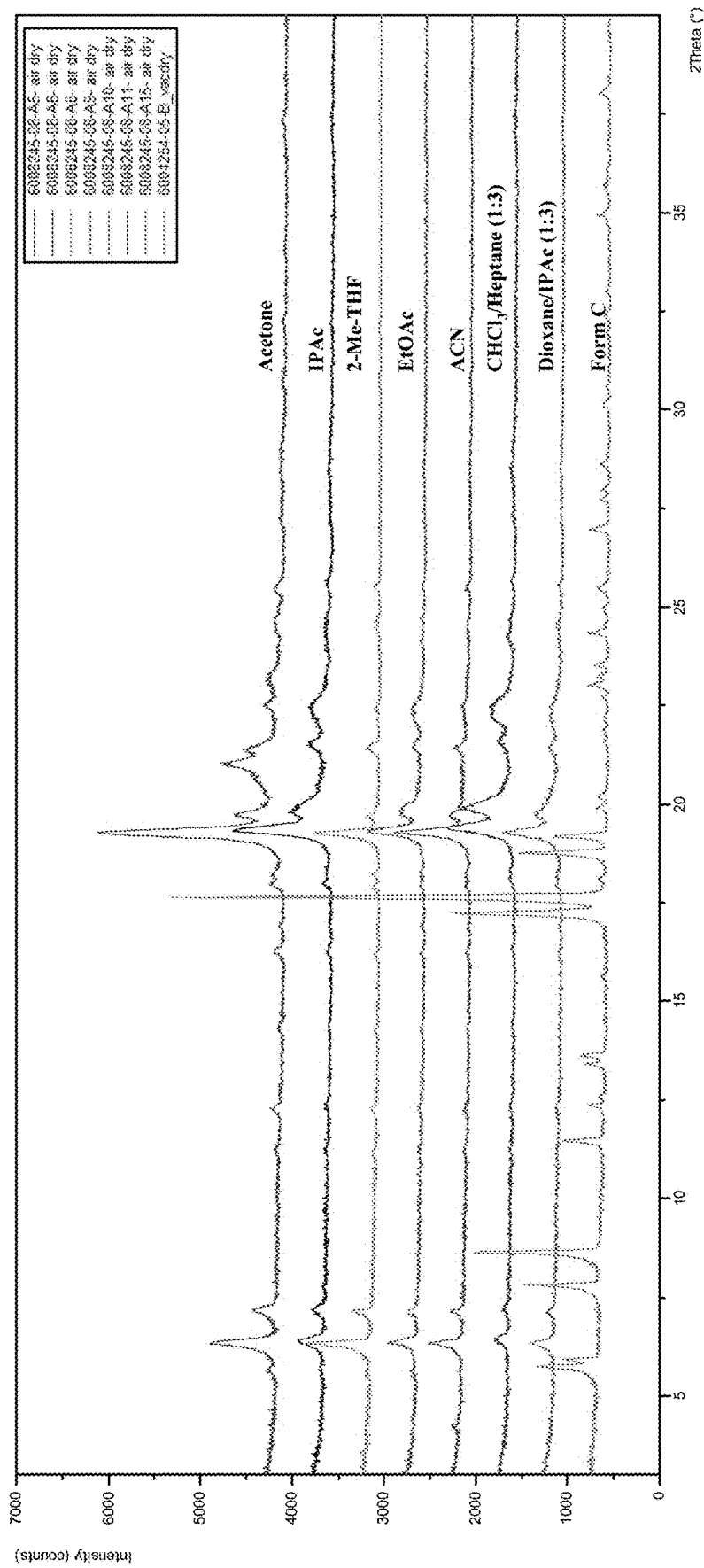
FIG. 8 sets forth an XRPD overlay of Form B from slow cooling experiments.
Figure 9:
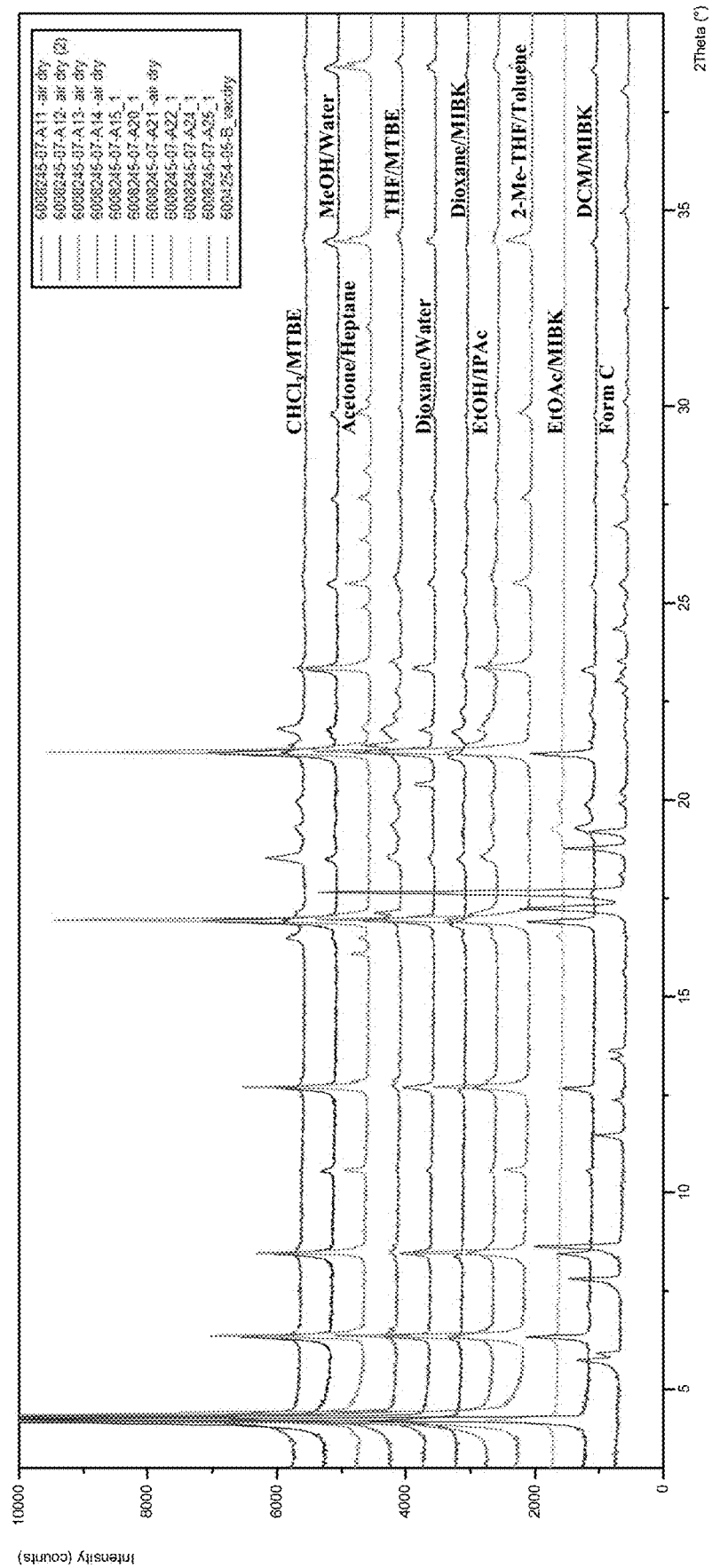
FIG. 9 sets forth an XRPD overlay of Form A from anti-solvent addition experiments.

Compound A was prepared for slow cooling experiments according to the methods described above. The resulting solids were analyzed by XRPD and identified for physical state (Table 12). Slow cooling experiments yielded Form A (FIG. 7) and Form B (FIG. 8).

TABLE 12

Summary of cooling experiments

| Temp | Solvent/Anti-solvent | Cmpd A (mg) | Solvent/Anti-solvent (mL) | Polymorph Form |
|---|---|---|---|---|
| 50° C.→RT→5° C.→−20° C. | Heptane | 16.9 | 1.0 | No material |
| 50° C.→RT→5° C.→−20° C. | Toluene | 15.3 | 1.0 | C |
| 50° C.→RT→5° C.→−20° C. | Water | 15.7 | 1.0 | No material |
| 50° C.→RT→5° C.→−20° C. | IPA | 15.4 | 1.0 | A |
| 50° C.→RT→5° C.→−20° C. | Acetone | 13.4 | 1.0 | B |
| 50° C.→RT→5° C.→−20° C. | IPAc | 15.8 | 1.0 | B |
| 50° C.→RT→5° C.→−20° C. | MIBK | 15.3 | 1.0 | C |
| 50° C.→RT→5° C.→−20° C. | 2-Me-THF | 12.9 | 1.0 | B |

TABLE 12-continued

Summary of cooling experiments

| Temp | Solvent/Anti-solvent | Cmpd A (mg) | Solvent/Anti-solvent (mL) | Polymorph Form |
|---|---|---|---|---|
| 50° C.→RT→5° C.→−20° C. | EtOAc | 14.6 | 1.0 | B |
| 50° C.→RT→5° C.→−20° C. | ACN | 15.8 | 1.0 | B |
| 50° C.→RT→5° C.→−20° C. | CHCl3/Heptane (1:3) | 18.3 | 1.0 | B |
| 50° C.→RT→5° C.→−20° C. | MeOH/Toluene (1:3) | 15.7 | 0.5 | C |
| 50° C.→RT→5° C.→−20° C. | THF/Water (1:3) | 15.1 | 1.0 | A |
| 50° C.→RT→5° C.→−20° C. | Acetone/MTBE (1:3) | 14.3 | 1.0 | A |
| 50° C.→RT→5° C.→−20° C. | Dioxane/IPAc (1:3) | 17.1 | 1.0 | B |

Example 13: Polymer Induced Crystallization

Compound A was prepared for polymer induced crystallization experiments according to the methods described above. The resulting solids were analyzed by XRPD and identified for physical state (Table 13).

TABLE 13

Summary of polymer experiments

| Temp. | Solvent | Cmpd A (mg) | Solvent (mL) | Polymer | Polymorph Form |
|---|---|---|---|---|---|
| RT | MeOH | 15.6 | 0.5 | HPMC-AS | C |
| RT | EtOH | 18.9 | 0.5 | MC | Amorphous + C |
| RT | Acetone | 17.4 | 0.5 | PVP-VA | Amorphous + C |
| RT | THF | 19.2 | 0.5 | PVA | Little material |
| RT | Dioxane | 14.7 | 0.5 | PVP | Amorphous |
| RT | ACN | 16.5 | 0.5 | HPMC-AS | C |
| RT | 2-Me-THF | 17.4 | 0.5 | MC | Amorphous |
| RT | CHCl3 | 15.3 | 0.5 | PVP-VA | Amorphous + C |
| RT | EtOAc | 14.8 | 0.5 | PVA | Type C |
| RT | MIBK | 18.5 | 0.5 | PVP | Amorphous + C |
| RT | IPA | 16.3 | 0.5 | HPMC-AS | Amorphous + C |
| RT | Toluene | 18.7 | 0.5 | MC | Amorphous + C |
| RT | IPAc | 18.6 | 0.5 | PVP-VA | Amorphous |
| RT | DCM | 17.1 | 0.5 | PVA | Amorphous |
| RT | CHCl3/ACN (1:1) | 18.5 | 0.5 | PVP | Amorphous |

Example 14: Anti-Solvent Crystallization

Figure 10:
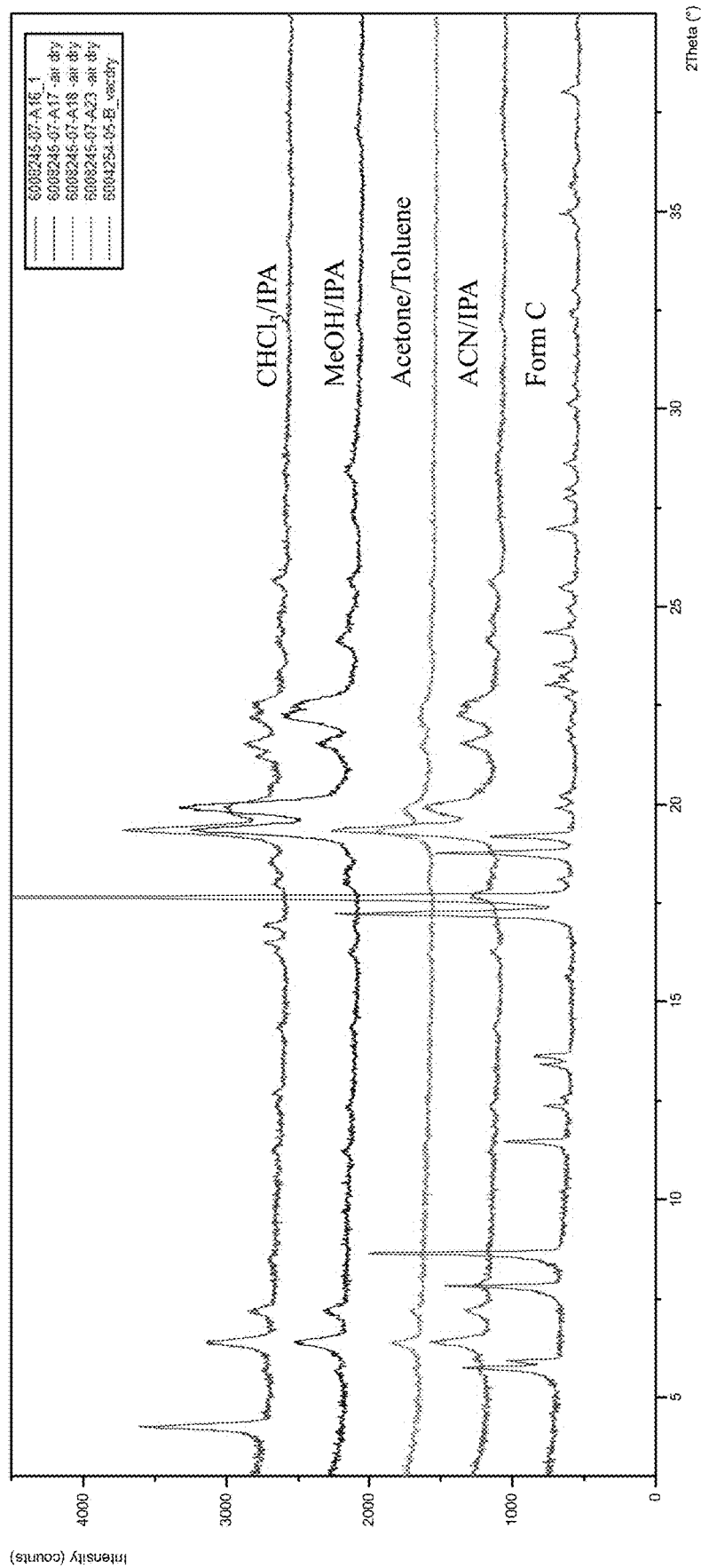
FIG. 10 sets forth an XRPD overlay of a mixture of Forms A and B (CHCl$_3$/IPA) and of Form B from anti-solvent addition experiments.
Figure 11:
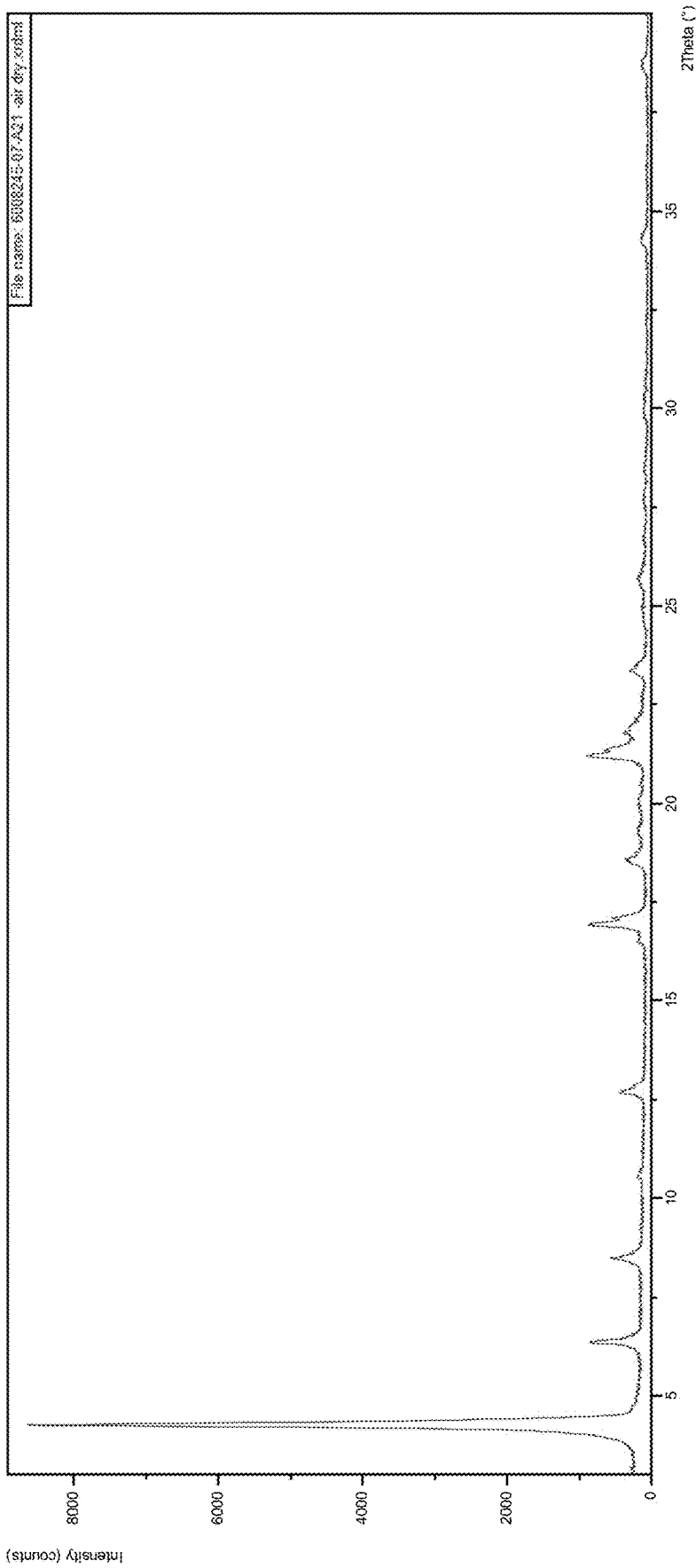
FIG. 11 sets forth an XRPD of Form A after air-drying.

Compound A was prepared for anti-solvent addition experiments according to the methods described above. The resulting solids were analyzed by XRPD and identified for physical state (Table 14). Most of the anti-solvent addition experiments yielded Form A (FIG. 9), Form A+B, and Form B (FIG. 10).

TABLE 14

Summary of anti-solvent experiments

| Solvent | Solvent (mL) | Anti-solvent | Anti-solvent (mL) | Polymorph Form |
|---|---|---|---|---|
| CHCl3 | 0.2 | MTBE | 4.0 | A |
| MeOH | 1.2 | Water | 3.2 | A |
| Acetone | 2.6 | Heptane | 5.0 | A |
| THF | 0.6 | MTBE | 4.0 | A |
| Dioxane | 1.6 | Water | 4.0 | A |
| CHCl3 | 0.2 | IPA | 4.0 | A + B |
| MeOH | 1.4 | IPAc | 4.0 | B |
| Acetone | 3.0 | Toluene | 5.0 | B |
| DCM | 0.1 | THF | 4.0 | Amorphous |
| Dioxane | 1.2 | MIBK | 4.0 | A |
| EtOH | 3.0 | IPAc | 5.0 | A |
| 2-Me-THF | 5.0 | Toluene | 7.0 | A |
| ACN | 3.0 | IPA | 4.0 | B |
| EtOAc | 5.0 | MIBK | 7.0 | A |
| DCM | 0.2 | MIBK | 4.0 | A |

Example 15: Characterization of Form A

Form A was obtained from multiple screening methods. A sample of Form A was obtained through anti-solvent addition (solvent: EtOH, anti-solvent: IPAc) at room temperature and analyzed by XRPD (Example 12 and FIG. 11).

Figure 12:
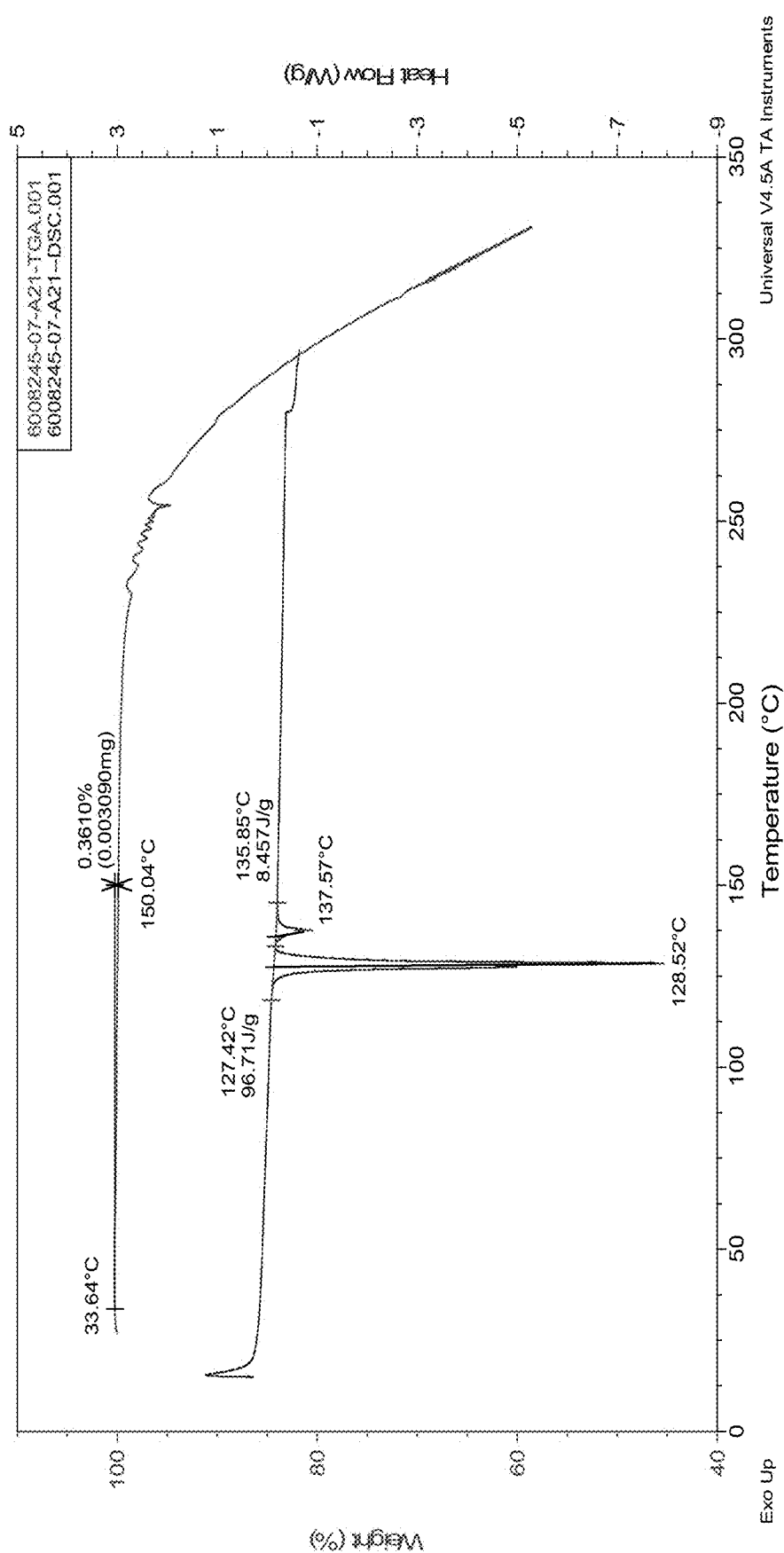
FIG. 12 sets forth a DSC/TGA overlay of Form A after air-drying.

DSC analysis showed that Form A displayed endotherms at 128.5° C. and 137.5° C. (FIG. 12). Form A showed 0.36% weight loss before 150° C. as measured by TGA.

Figure 13:
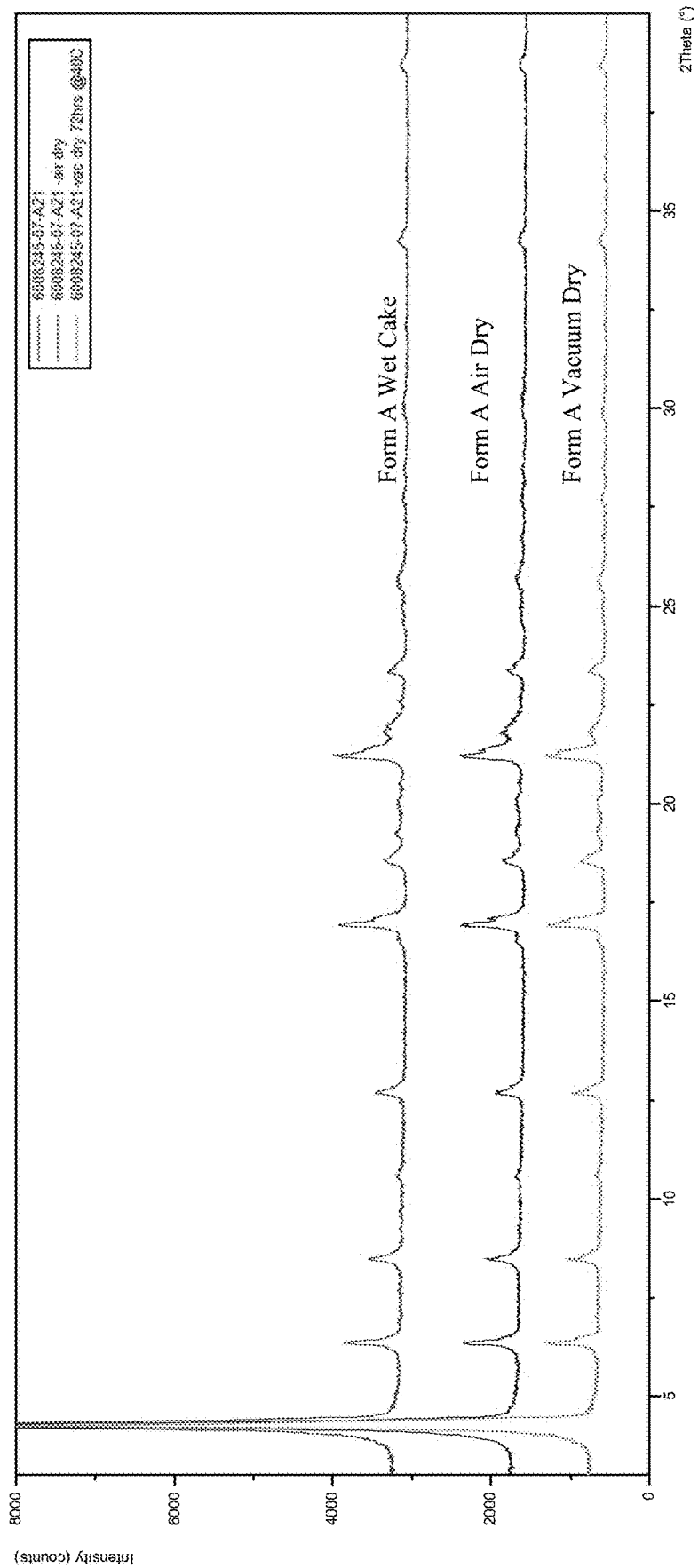
FIG. 13 sets forth an XRPD of Form A (wet cake, air dry and vacuum dry).
Figure 14:
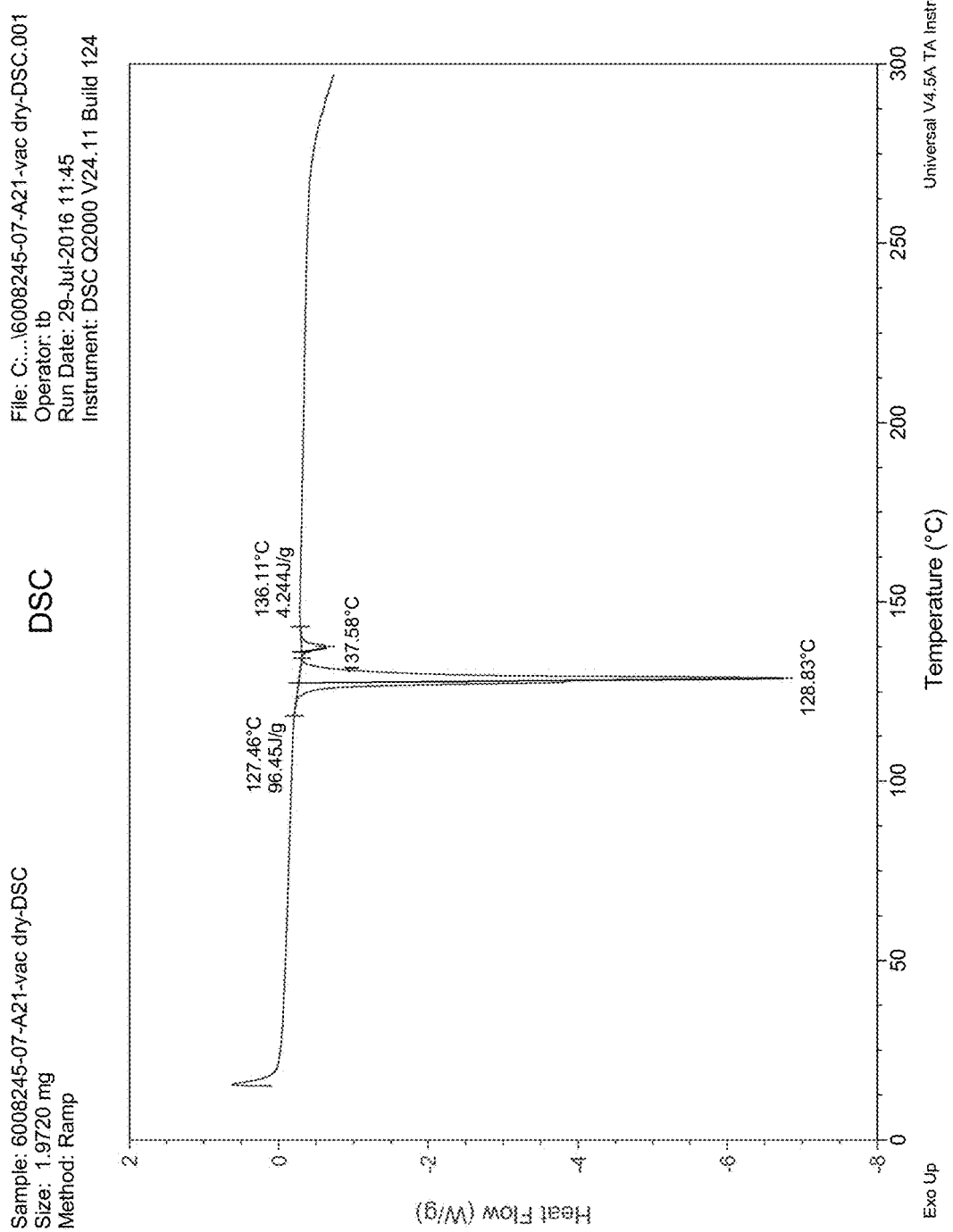
FIG. 14 sets forth a DSC thermogram of Form A after vacuum drying.

Form A showed no loss of crystallinity after air-drying or vacuum drying as measured by XRPD (FIG. 13). DSC analysis showed that Form A (vacuum dried) displayed no change from the air-dried sample (FIG. 14).

Example 16: Characterization of Form B

Figure 15:
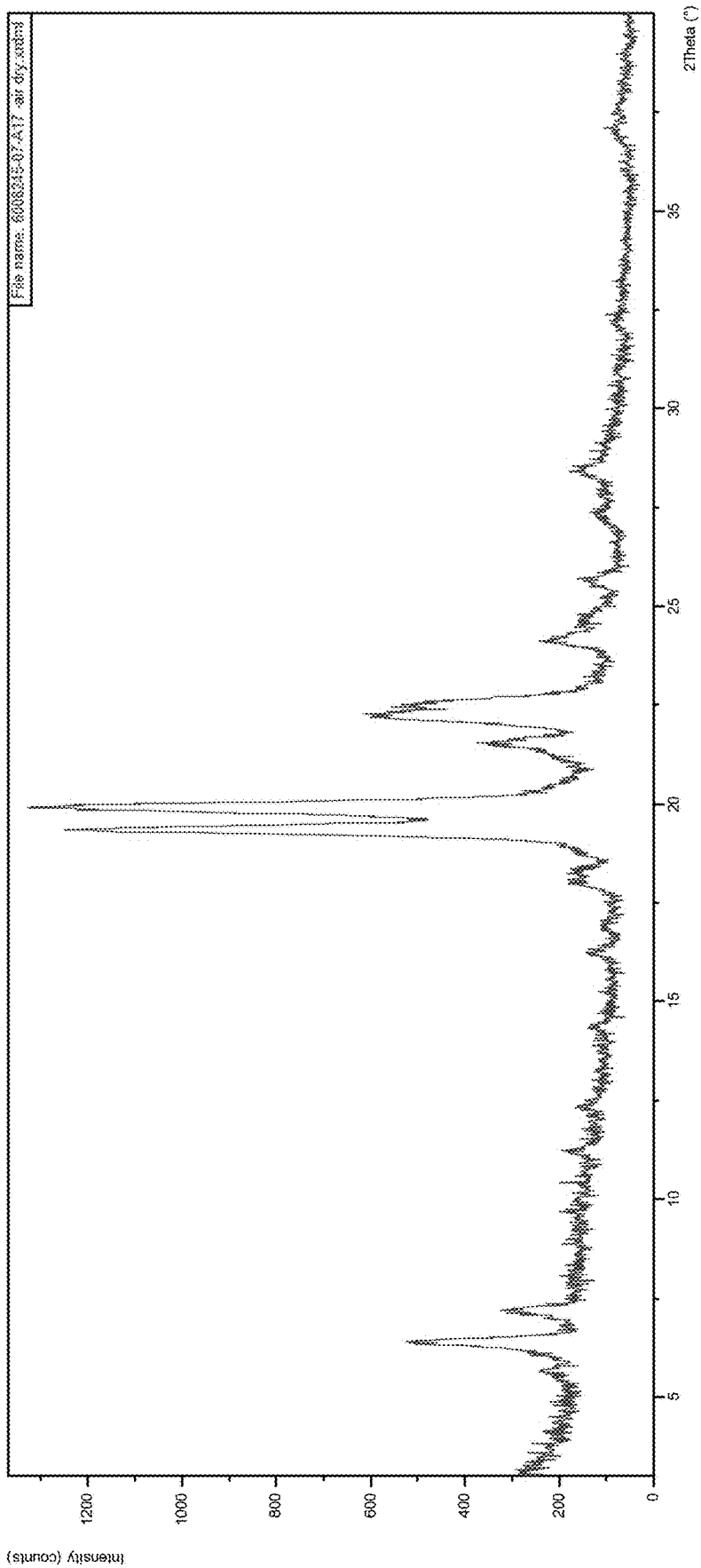
FIG. 15 sets forth an XRPD of Form B.

Form B was obtained from multiple screening methods. An example from anti-solvent addition (solvent: MeOH, anti-solvent: IPAC) is shown in FIG. 15.

Figure 16:
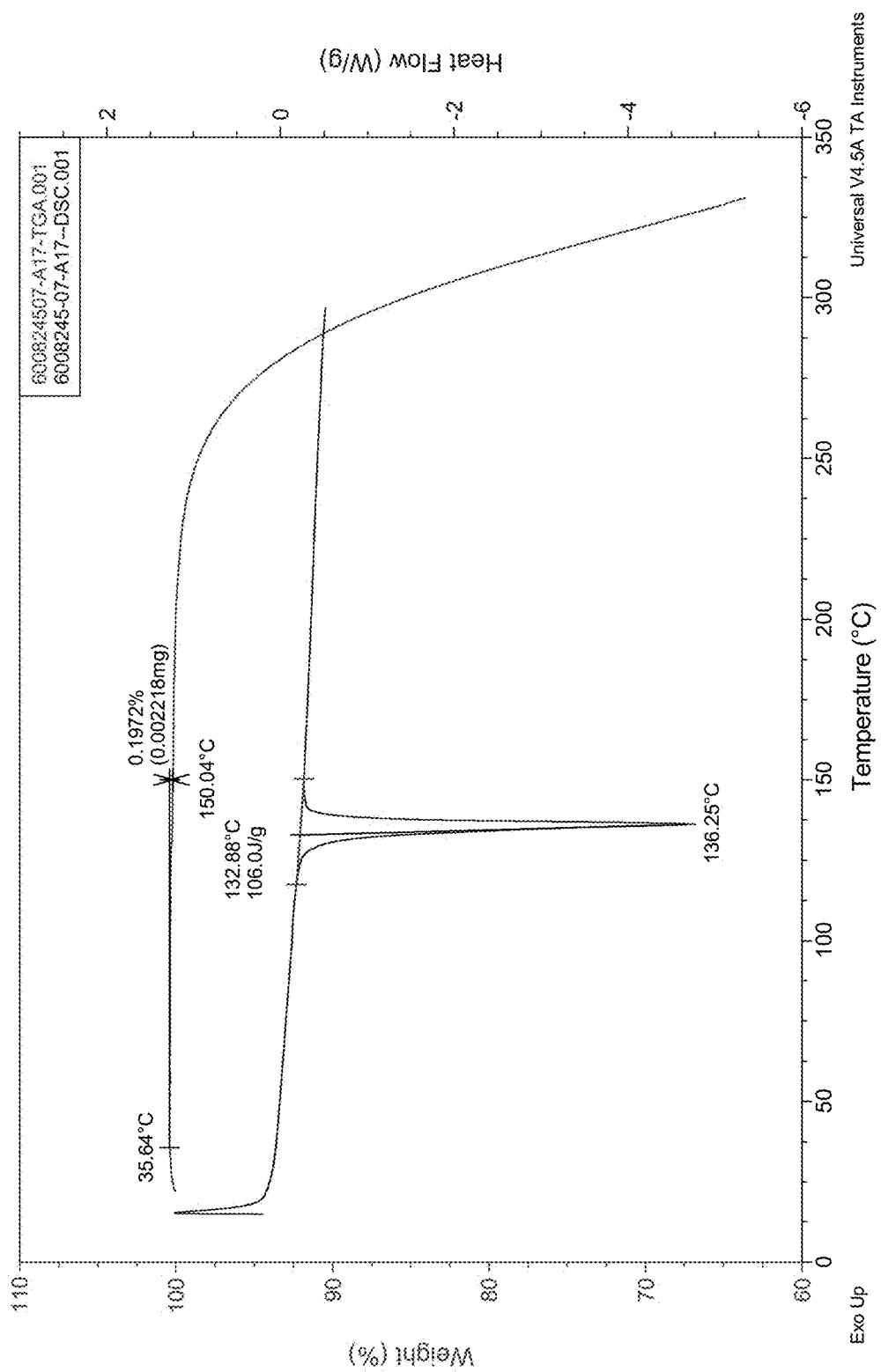
FIG. 16 sets forth a DSC/TGA overlay of Form B.

DSC analysis showed that Form B displayed an endotherm at 136° C. (FIG. 16). TGA analysis showed 0.20% weight loss before 150° C.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A Form B polymorph of Compound A:

(A)

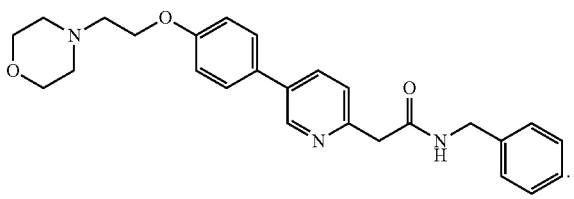 [SMILES: O=C(Cc1ccc(-c2ccc(OCCN3CCOCC3)cc2)cn1)NCc1ccccc1]

characterized by having X-ray powder diffraction peaks at approximately 6.4, 19.3, and 19.9 °2θ using Cu Kα radiation.

2. The Form B polymorph of claim 1, characterized by having X-ray powder diffraction peaks at approximately 6.4, 7.2, 19.3, 19.9, 21.6, 22.1, and 22.6 °2θ using Cu Kα radiation.

3. The Form B polymorph of claim 1, characterized by having an X-ray powder diffraction pattern substantially similar to that set forth in FIG. 1, 6, 8, 10, 15, or 20.

4. The Form B polymorph of claim 1, characterized by an endothermic event with onset at between approximately 133° C. and approximately 138° C. as measured by DSC.

5. The Form B polymorph of claim 1, characterized by a DSC thermogram substantially similar to that set forth in FIG. 16.

6. The Form B polymorph of claim 1, characterized by a weight loss of approximately 0.20% between about 33° C. and about 150° C., as measured by TGA.

7. A pharmaceutical composition comprising a polymorph of claim 1 and a pharmaceutically acceptable carrier or excipient.

8. The Form B polymorph of claim 1, characterized by having X-ray powder diffraction peaks at approximately 6.4, 7.2, 19.3, 19.9, 21.6, 22.1, 22.6, and 24.2 °2θ using Cu Kα radiation.

9. The Form B polymorph of claim 1, characterized by having an X-ray powder diffraction pattern substantially similar to that set forth in FIG. 15.

10. The Form B polymorph of claim 1, characterized by an endothermic event with onset at approximately 136° C. as measured by DSC.

* * * * *